(12) United States Patent (10) Patent No.: US 9,026,208 B2
Morley et al. (45) Date of Patent: May 5, 2015

(54) METHOD AND SYSTEM FOR IMPROVING IMPEDANCE DATA QUALITY IN THE PRESENCE OF PACING PULSES

(71) Applicant: Pacesetter, Inc., Sylmar, CA (US)

(72) Inventors: Bruce A. Morley, Acton, CA (US); Gene A. Bornzin, Simi Valley, CA (US); Kritika Gupta, San Francisco, CA (US); Rupinder Bharmi, Canyon Country, CA (US); Laurence S. Sloman, West Hollywood, CA (US); Edward Karst, Los Angeles, CA (US); Wenbo Hou, Valencia, CA (US); Riddhi Shah, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 40 days.

(21) Appl. No.: 13/776,494

(22) Filed: Feb. 25, 2013

(65) Prior Publication Data

US 2014/0243917 A1    Aug. 28, 2014

(51) Int. Cl.
| | |
|---|---|
| *A61N 1/365* | (2006.01) |
| *A61N 1/39* | (2006.01) |
| *A61B 5/00* | (2006.01) |
| A61N 1/362 | (2006.01) |
| A61B 5/053 | (2006.01) |
| A61N 1/368 | (2006.01) |

(52) U.S. Cl.
CPC .............. *A61N 1/3962* (2013.01); *A61N 1/3621* (2013.01); *A61B 5/0535* (2013.01); *A61B 5/0538* (2013.01); *A61N 1/36521* (2013.01); *A61N 1/3684* (2013.01); *A61B 5/686* (2013.01); *A61B 5/7217* (2013.01)

(58) Field of Classification Search
CPC ............ A61N 1/3627; A61N 1/36521; A61N 1/3625; A61N 1/365; A61N 1/36514; A61N 1/36564
USPC ...................................................... 607/17–20
See application file for complete search history.

(56) References Cited

U.S. PATENT DOCUMENTS

| | | | |
|---|---|---|---|
| 5,999,854 A * | 12/1999 | Deno et al. ....................... 607/18 |
| 7,653,436 B2 | 1/2010 | Schecter | |
| 7,680,536 B2 | 3/2010 | Sathaye et al. | |
| 8,050,760 B2 | 11/2011 | Cholette | |
| 2009/0030471 A1* | 1/2009 | Rousso et al. ................... 607/27 |
| 2012/0010516 A1 | 1/2012 | Cholette | |
| 2012/0136406 A1 | 5/2012 | Min | |

* cited by examiner

*Primary Examiner* — Rex R Holmes

(57) ABSTRACT

An implantable medical device, comprised of at least one lead configured to be located proximate to a heart, the at least one lead including electrodes, at least a portion of the electrodes configured to sense cardiac activity. A therapy module configured to control delivery of pacing pulses in accordance with a therapy timing and based on the cardiac sensed activity sensed. Cardiac impedance (CI) sensor circuitry configured to be coupled to at least a first combination of the electrodes to sense cardiac impedance (CI), the CI sensor circuitry generating an impedance data stream associated with a corresponding CI sensing vector.

16 Claims, 11 Drawing Sheets

METHOD AND SYSTEM FOR IMPROVING IMPEDANCE DATA QUALITY IN THE PRESENCE OF PACING PULSES

BACKGROUND OF THE INVENTION

Embodiments of the present invention generally relate to measuring cardiac impedance, and more particularly to methods, devices and systems that improve cardiac impedance measurement signal quality in the presence of pacing pulses.

Implantable medical devices (IMD) are well known in the art. The IMD may take the form of implantable defibrillators or cardioverters which treat accelerated rhythms of the heart such as fibrillation. The IMD may also take the form of implantable pacemakers which maintain the heart rate above a prescribed limit, such as, for example, to treat a bradycardia. Implantable medical devices may also incorporate more than one of a pacemaker, a cardioverter and a defibrillator. Defibrillators may include "shock only" functionality or, in addition to shocking functionality, a defibrillator may be capable of providing cardiac resynchronization therapy (CRT) functionality.

IMDs are coupled to one or more leads that include electrodes to sense one or more types of information and to deliver various types of therapy. The IMDs typically include various sensing circuitry and logic that monitor a heart for cardiac signals, and analyzes the cardiac signals to identify normal sinus rhythm, arrhythmias and the like. The sensing circuits sense cardiac activity for the detection of intrinsic cardiac events such as intrinsic atrial events (P-waves) and intrinsic ventricular events (R-waves). By monitoring P-waves and/or R-waves, the IMD circuits are able to determine the intrinsic rhythm of the heart and provide stimulation pulses that force atrial and/or ventricular depolarizations at appropriate times in the cardiac cycle when required to help stabilize the electrical rhythm of the heart.

IMDs also include sensing circuitry and logic that utilize impedance cardiograph, such as for the purpose of monitor hemodynamic output. Intracardiac impedance recordings, such as using trans-venously implanted leads, are now being used in implantable devices. The IMD collects impedance data in various manners. For example, one approach is to deliver small short current bursts between two electrodes proximate to the heart and simultaneously measure a voltage potential between the same electrodes or different electrodes. The current source and voltage potential are used to derive impedance data. The impedance data is collected over one or more cardiac cycles to monitor a hemodynamic output of the heart.

However, certain limitations exist today in connection with collecting impedance data, given that the IMD collects impedance data, while the same IMD performs normal sensing and pacing operations. The pacing pulses from the IMD (e.g., pacemakers, ICD, CRT, etc.) may interfere with the recording of impedance data. The effect on the impedance data may include crosstalk from the pacing pulse or loss of impedance measurement due to disconnection of the impedance sensing circuitry during pacing pulse delivery. In general, the change of intracardiac impedance (e.g., the maximum and minimum dynamic range of impedance data recorded per cardiac cycle) varies in the order of 0.2 ohms to 1.5 ohms between peak and valley measurements. Given such a small dynamic range, even small artifacts, such as related to hardware crosstalk or post-pace blanking, discharge and recharge, fall within the impedance range and can impact the fidelity, signal morphology and hence the IMD's utility as a sensor to derive hemodynamic information.

SUMMARY

In accordance with one embodiment, an implantable medical device is provided, comprised of at least one lead configured to be located proximate to a heart, the at least one lead including electrodes, at least a portion of the electrodes configured to sense cardiac activity. A therapy module is configured to control delivery of pacing pulses in accordance with a therapy timing and based on the cardiac sensed activity sensed. A cardiac impedance (CI) sensor circuitry is configured to be coupled to at least a first combination of the electrodes to sense cardiac impedance (CI). The CI sensor circuitry generates an impedance data stream associated with a corresponding CI sensing vector. A CI module is configured to manage the CI sensor circuitry to collect impedance data during active CI collection windows. An artifact reduction (AR) module is configured to at least one of: (A) manage at least one of (i) the therapy timing of the therapy module and (ii) the active CI collection windows, to avoid delivery of the pacing pulses during the active CI collection windows during which the CI sensor circuitry collects impedance data; and (B) identify a reconstruction region in the impedance data and reconstruct a sample sub-set of the impedance data that occurs during the reconstruction region to at least partially remove artifacts in the impedance data stream associated with a pacing pulse.

Optionally, the AR module designates a beginning of the reconstruction region based on a time at which a corresponding pacing pulse is delivered, the reconstruction region having a predetermined artifact duration. The reconstruction region has an artifact duration based on a width of the pacing pulse, a blanking interval following the pacing pulse, and a coupling capacitor discharge interval associated with the pacing pulse.

Optionally, the AR module is configured to replace the sample sub-set of the impedance data that occurs during the reconstruction region, with a synthetic sample sub-set by at least one of: (A) applying a polynomial fit equation that connects valid sample sub-sets before and after the reconstruction region to bridge the reconstruction region; (B) applying interpolation to connect valid sample sub-sets before and after the reconstruction region to bridge the reconstruction region; and C) applying a sinusoidal curve fitting filter to the impedance data before, within and after the reconstruction regions.

The AR module may be configured to apply at least one of high and low pass filters to the impedance data, the at least one of high and low pass filters having filter characteristics configured to at least partially correct for artifacts in the sample sub-set collecting while delivering a pacing pulse.

The AR module may align the reconstruction region to overlap in time with at least one of: (A) a time at which pacing pulses are delivered in an atrium; (B) a time at which pacing pulses are delivered in a ventricle; (C) a blanking interval following the pacing pulses; (D) a settling time associating with IC sensor circuitry; and (E) a time at which capacitance is discharged from a coupling capacitor following the pacing pulses.

The CI module may be configured to manage the CI sensor circuitry by turning the CI sensor circuitry ON and OFF during periodic sample intervals. Each of the sample intervals has an active segment in which the CI sensor circuitry is ON and generates a corresponding sample sub-set of the impedance data. Each of the sample intervals has an inactive segment in which the CI sensor circuitry is OFF and does not generate the impedance data. The CI module processing the impedance data collected over at least one cardiac cycle to provide an impedance sample set for the at least one cardiac cycle.

The therapy module may be configured to control discharge of a coupling capacitor electrically connected in series with a first electrode that delivers the pacing pulses, the therapy module managing a time at which the coupling capacitor discharges to interleave discharge of the coupling capacitor between active segments of the sample interval.

The AR module may be configured to manage the therapy timing to interleave the pacing pulses between the active CI collection windows. The AR module is configured to manage the active CI collection windows by shifting the active CI collection windows relative to the pacing pulses to avoid overlap of the pacing pulses and the active CI collection windows.

The CI sensor circuitry may be configured to turn ON and OFF during periodic sample intervals. Each of the sample intervals has an active segment in which a sample sub-set of the impedance data is collected, each of the sample intervals having an inactive segment in which sample sub-sets are not generate. The therapy module manages a time at which the pacing pulse is delivered to interleave the pacing pulse between active segments of the sample interval. The CI sensor circuitry may be configured to turn ON and OFF during periodic sample intervals, each of the sample intervals having an active segment in which a sample sub-set of the impedance data is collected, each of the sample intervals having an inactive segment in which sample sub-sets are not collected. The therapy module manages a time at which a coupling capacitor discharges to overlap discharge of the coupling capacitor with the inactive segments of the sample intervals. The coupling capacitor accumulates a coupling charge in connection with delivery of the pacing pulse. The therapy module controls the coupling capacitor to discharge the coupling charge in a separated divided manner over multiple inactive segments of the sample intervals.

In accordance with one embodiment, a method is provided for processing impedance data sensed by an implantable medical device (IMD), the IMD having at least one lead configured to be located proximate to a heart, the at least one lead including electrodes, at least a portion of the electrodes configured to sense cardiac activity. The method comprises controlling delivery of pacing pulses in accordance with a therapy timing and based on cardiac activity sensed; providing a cardiac impedance (CI) sensor channel configured to be coupled to at least a first combination of the electrodes to sense cardiac impedance; and generating an impedance data stream, over the CI sensor channel, associated with a corresponding CI sensing vector. The method manages the CI sensor channel to collect impedance data during active CI collection windows; and perform artifact reduction (AR) by at least one of: (A) manage at least one of (i) the therapy timing and (ii) the active CI collection windows, to avoid delivery of the pacing pulses during the active CI collection windows during which the CI sensor channel collects impedance data; and; (B) identify a reconstruction region in the impedance data and reconstruct a sample sub-set of the impedance data that occurs during the reconstruction region to at least partially remove artifacts in the impedance data stream associated with a pacing pulse.

The AR operation may designate a beginning of the reconstruction region based on a time at which a corresponding pacing pulse is delivered, the reconstruction region having a predetermined artifact duration. The reconstruction region has an artifact duration based on a width of the pacing pulse, a blanking interval following the pacing pulse, and a coupling capacitor discharge interval associated with the pacing pulse.

The AR operation may include replacing the sample sub-set of the impedance data that occurs during the reconstruction region, with a synthetic sample sub-set by at least one of: (A) applying a polynomial fit equation that connects valid sample sub-sets before and after the reconstruction region to bridge the reconstruction region; (B) applying interpolation to connect valid sample sub-sets before and after the reconstruction region to bridge the reconstruction region; and C) applying a sinusoidal curve fitting filter to the impedance data before, within and after the reconstruction regions.

The AR operation may include applying at least one of high and low pass filters to the impedance data, the at least one of high and low pass filters having filter characteristics configured to at least partially correct for artifacts in the sample sub-set collecting while delivering a pacing pulse.

The AR operation may include aligning the reconstruction region to overlap in time with at least one of: (A) a time at which pacing pulses are delivered in an atrium; (B) a time at which pacing pulses are delivered in a ventricle; (C) a blanking interval following the pacing pulses; (D) a settling time associating with IC sensor circuitry; and (E) a time at which capacitance is discharged from a coupling capacitor following the pacing pulses.

The CI sensor channel managing operation may include turning the CI sensor channel ON and OFF during periodic sample intervals, each of the sample intervals having an active segment in which the CI sensor channel is ON and generates a corresponding sample sub-set of the impedance data, each of the sample intervals having an inactive segment in which the CI sensor channel is OFF and does not generate the impedance data, the impedance data collected over at least one cardiac cycle being processed to provide an impedance sample set for the at least one cardiac cycle. The method further comprises controlling discharge of a coupling capacitor electrically connected in series with a first electrode that delivers the pacing pulses, and managing a time at which the coupling capacitor discharges to interleave discharge of the coupling capacitor between active segments of the sample interval.

The AR operation may include managing the therapy timing to interleave the pacing pulses between the active CI collection windows. The AR operation may manage the active CI collection windows by shifting the active CI collection windows relative to the pacing pulses to avoid overlap of the pacing pulses and the active CI collection windows. The method further comprises turning ON and OFF the CI sensor circuitry during periodic sample intervals, each of the sample intervals having an active segment in which a sample sub-set of the impedance data is collected, each of the sample intervals having an inactive segment in which sample sub-sets are not generate. The controlling operation may include managing a time at which the pacing pulse is delivered to interleave the pacing pulse between active segments of the sample interval.

Optionally, the CI sensor channel is turned ON and OFF during periodic sample intervals, each of the sample intervals having an active segment in which a sample sub-set of the impedance data is collected, each of the sample intervals having an inactive segment in which sample sub-sets are not collected. The controlling operation may include managing a time at which a coupling capacitor discharges to overlap discharge of the coupling capacitor with the inactive segments of the sample intervals. Further comprises accumulating a coupling charge on the coupling capacitor in connection with delivery of the pacing pulse, the controlling operation including controlling the coupling capacitor to discharge the coupling charge in a separated divided manner over multiple inactive segments of the sample intervals.

DETAILED DESCRIPTION

Figure 1:
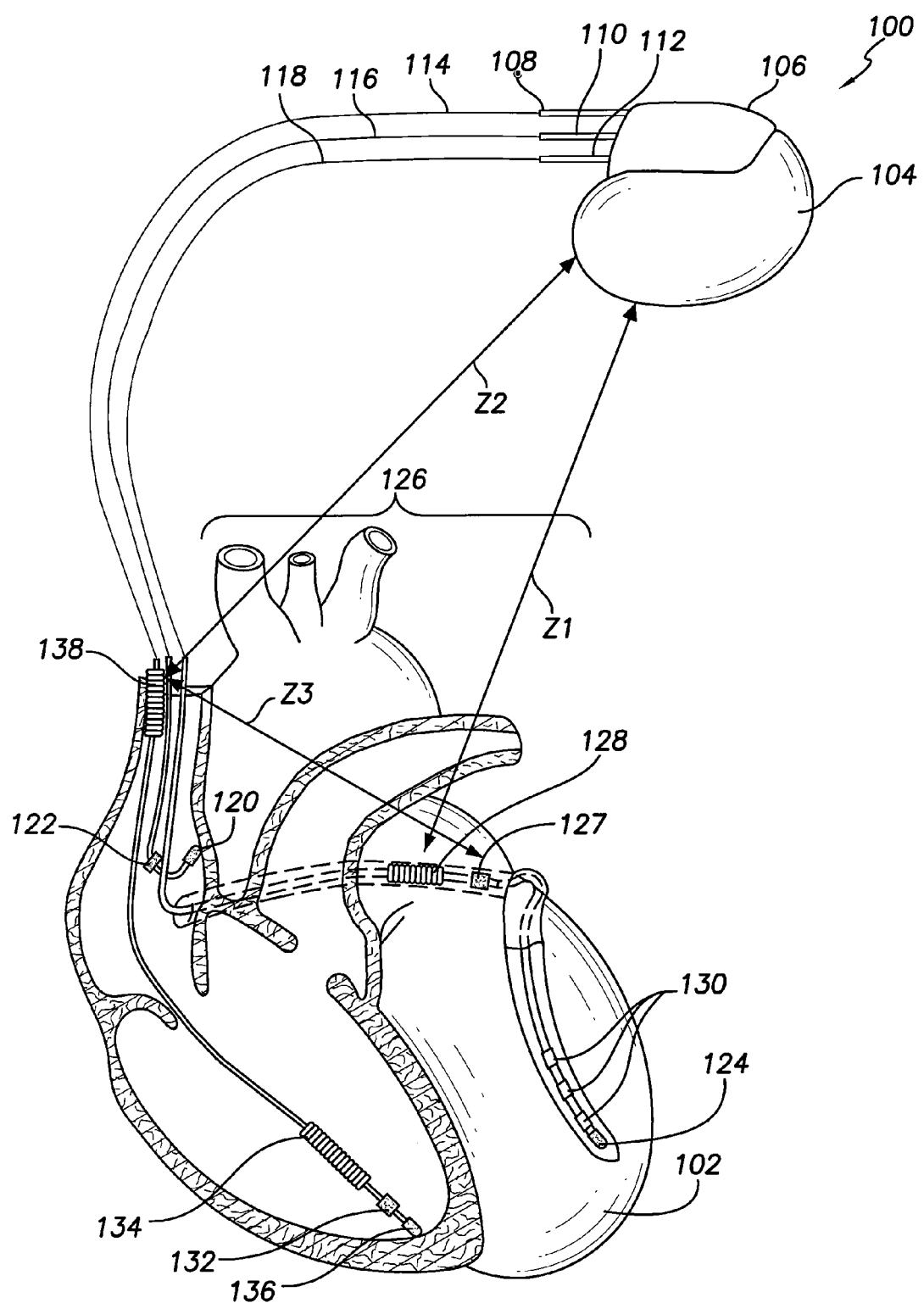
FIG. 1 illustrates an IMD or external device that is coupled to a heart in accordance with an alternative embodiment.

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In the context of this application, the term "impedance" refers to the relatively low frequency component of the impedance. The impedance is calculated as $z=u/i$, where u is the measured voltage and i is the applied excitation current.

The term "cardiac impedance" is the impedance calculated based on current or voltage measurements between electrodes that are located inside or outside of the four chambers of the heart. Cardiac impedance may be collected based on measurements taken along one or more impedance vectors that extends through at least a portion of the greater vessels and/or through one or more chambers of the heart. The "cardiac impedance" may be described as having an offset generally known as Zo. The great vessels or chamber(s) of interest may be juxta-positioned between the measuring electrodes. In addition, the process of breathing modulates the signal as well because the electrodes move with each breath and because air is brought into the lungs raising the impedance with each inspiration. These relatively low frequency signals may be high pass filtered at about 0.7 to reject respiration which typically has frequency components of less than 0.2 to 0.35 hertz, while the cardiac ejections have frequency components starting at about 0.7 hertz to about 14 hertz, which may also be referred to as cardiogenic impedance or dynamic cardiac impedance. The cardiac component of Z is typically in the range about 0.5 to 4% of Zo and is in the range of 0.25 to 2 ohms.

The term "impedance data", as used throughout shall refer to any of voltage, impedance or current values (analog or digital) measured by the CI sensing circuitry and/or along CI sensing channel. The voltage, impedance or current values are collected along a corresponding impedance vector between predetermined combinations of the electrodes to monitor cardiac output and determine whether sufficient or insufficient cardiac output (CO) and/or hemodynamic performance exists.

The term "hemodynamic performance" is comprised of at least one of cardiac output, systolic blood pressure, diastolic blood pressure, contractility, stroke volume, systolic time, and Q-wave to onset of systole, QRS to onset of systole. The term "therapy timing" refers to parameters associated with one or more of AV delay, V-V delay, stimulation rate, stimulating electrodes chosen for pacing, pulse combinations, stimulation lead configuration and the like.

The term "sample sub-set" may refer to one or more samples. Hence, in certain embodiments, a sample sub-set may include only a single sample.

FIG. 1 illustrates an IMD 100 or external device that is coupled to a heart 102. The IMD 100 may be a cardiac pacemaker, an ICD, a defibrillator, an ICD coupled with a pacemaker, and the like, implemented in accordance with one embodiment. The IMD 100 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings.

The IMD 100 includes a housing 305 that is joined to a header assembly 106 (e.g., an IS-4 connector assembly) that holds receptacle connectors 108, 110, 112 that are connected to a right ventricular lead 114, a right atrial lead 116, and a coronary sinus lead 118, respectively. The leads 114, 116 and 118 may be located at various locations, such as an atrium, a ventricle, or both to measure the physiological condition of the heart 102. One or more of the leads 114, 116 and 118 detect IEGM cardiac signals that form an electrical activity indicator of myocardial function over multiple cardiac cycles. To sense atrial cardiac signals and to provide right atrial chamber stimulation therapy, the right atrial lead 116 has at least an atrial tip electrode 120, which typically is implanted in the right atrial appendage, and an atrial ring electrode 122. The IEGM signals represent analog signals that are subsequently digitized and analyzed to identify waveforms or segments of interest. Examples of waveforms or segments of interest identified from the IEGM signals include the P-wave, T-wave, the R-wave, the QRS complex, the ST segment, and the like. The waveforms of interest may be collected over a period of time.

The coronary sinus lead 118 receives atrial and ventricular cardiac signals and delivers left ventricular pacing therapy using at least a left ventricular ("LV") tip electrode 124, and delivers left atrial ("LA") pacing therapy using at least a left atrial ring electrode 127. The coronary sinus lead 118 also is connected with one or more LV electrodes 130 disposed between the LV tip electrode 124 and the left atrial ring electrode 127. The LV electrodes 130 may be used as pacing and/or defibrillation electrodes. The LV electrodes 130 may be electrically common or separated to perform pacing and sensing operations independent of one another. The right ventricular ("RV") lead 114 has an RV tip electrode 136, an RV ring electrode 132, an RV coil electrode 134, and an SVC coil electrode 138. The RV lead 114 is capable of receiving cardiac signals, and delivering stimulation in the form of pacing, CRT and shock therapy to the right ventricle. The RV coil electrode 134 may be used as a pacing and/or defibrillation electrode. The housing 305 may also function as an electrode.

As explained herein, the IMD 100 measures/collects impedance data to monitor and determine variations in the cardiac output. Various combinations of the above noted electrodes (and/or alternative electrodes) are used to define an impedance vector and to collect impedance data along a path (e.g., a generally linear path) between the electrodes. One or more impedance vectors measured by the IMD 100 may extend through the greater vessels 126. The impedance vectors that extend through the greater vessels 126 represent the impedance of the tissue and the blood along the paths of the corresponding impedance vector(s). By way of example only, the impedance vectors measured by the IMD 100 may include one or more of first, second and third CI impedance vectors Z1, Z2 and Z3. The first and second CI impedance vectors Z1 and Z2 are between the housing 305 and SVC coil electrode 138 and the housing 305 and LA electrode 128, respectively. The third CI impedance vector Z3 is between the LA ring electrode 127 and SVC coil electrode 138. Alternative impedance vectors may be utilized.

The IMD 100 may collect impedance data using a four terminal measurement technique in one embodiment. The four terminal measurement technique may reduce the impact that the intrinsic impedance of the electrodes has on the impedance vector. The intrinsic impedances of the electrodes 124-138 may be large when compared to the change $\Delta Z$ in the impedance of the greater vessels. For example, the LV and RV electrode tips 124, 136 may have intrinsic impedances of 500 ohms or more while the change $\Delta Z$ in impedance of the myocardium in the greater vessels may be approximately 50 ohms or less. The four terminal measurement technique may eliminate the intrinsic impedances of the electrodes from the measured impedance vector.

The four terminal measurement technique involves applying a source current across a predetermined combination of electrodes, while simultaneously measuring a voltage between a different combination of the electrodes. With reference to the example of FIG. 1, the current may be supplied between the RV coil electrode 134 and the LV electrodes 130, while the voltage is measured between the SVC coil 138 and housing 305. The voltage measurement represents "impedance data" (also referred to as an impedance related voltage difference measurement) because the measured voltage and the known source current are used to calculate an impedance data value. Alternative combinations of electrodes may be used as the current source and/or to measure the impedance related voltage potential. For example, the same electrodes may be used to deliver the current source and to measure the voltage. Optionally, impedance data may be obtained using other techniques. As one example, impedance values may be directly measured.

Figure 2:
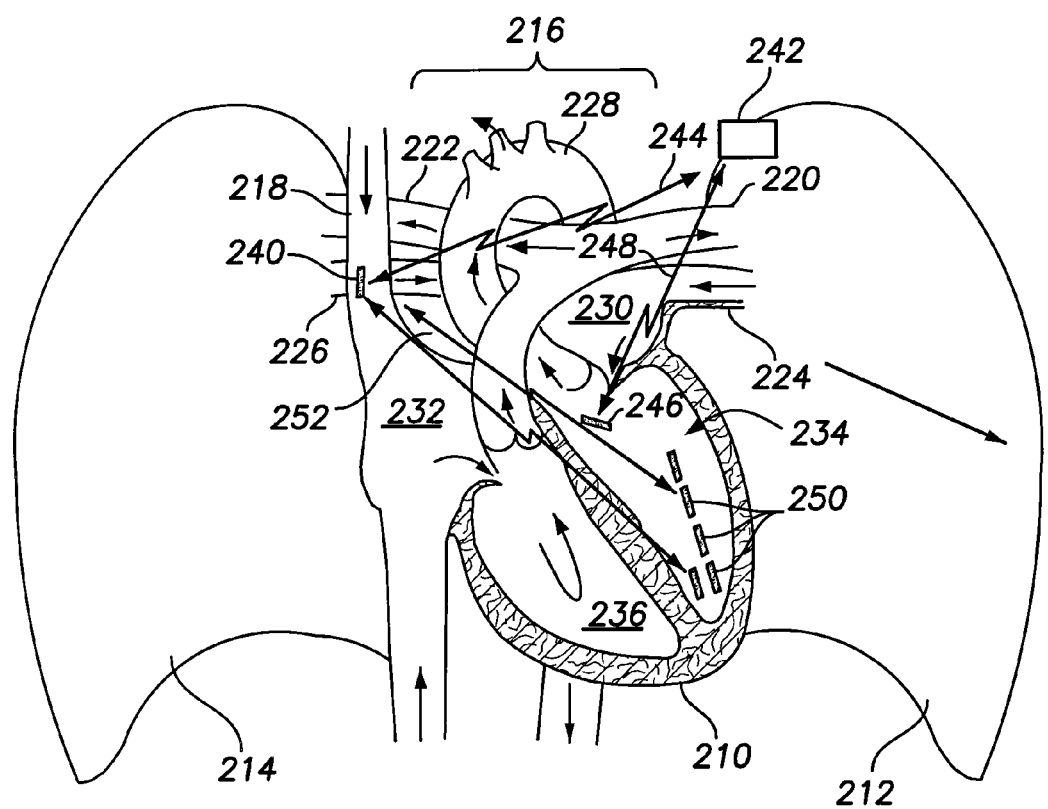
FIG. 2 illustrates a graphical representation a heart and impedance vectors that may be used in accordance with an alternative embodiment.

FIG. 2 illustrates a graphical representation a heart and impedance vectors that may be used in accordance with an alternative embodiment. FIG. 2 illustrates various locates at which electrodes may be located outside of, but proximate to the heart, as well as at locations outside and remote from the heart. Electrodes are positioned at these locations to measure impedance data. An IMD or an external PSA analyzer having an impedance plethysmograph then performs a hemodynamic assessment based on the impedance measurements. FIG. 2 illustrates the heart 210 between the left and right lungs 212 and 214. The direction of blood flow is noted by various arrows.

FIG. 2 also illustrates a portion of the greater vessels (generally denoted at 216) through which blood flows during entry to and exit from the heart 210. The greater vessels 216 generally include the superior vena cava (SVC) 218, the aorta 228, the pulmonary arteries 220 and 222, and the pulmonary veins 224 and 226. The greater vessels also include the left and right brachiocephalic arteries and veins, the left common carotid artery and left subclavian artery (not shown) which branch from the aorta 228. The heart 210 includes left and right atrium 230 and 232, and left and right ventricles 234 and 236.

In accordance with embodiments described herein, a lead assembly of one or more leads is provided having electrodes positioned inside and/or outside of the heart 210 and located such that a desired part of one or more chambers and/or a portion of the greater vessels 216 are interposed between the electrodes. It is understood that a combination of leads may be utilized in which electrodes are positioned as illustrated in FIG. 2 and electrodes are positioned as illustrated in FIG. 1. By way of example, an extra-cardiac (EC) electrode may be positioned at the superior vena cava 218, as denoted at EC electrode location 240. When an electrode is positioned at location 240, the electrode is outside of the heart 210, but proximate to the SVC 218, as well as proximate to the aorta 228, pulmonary veins 222 and pulmonary arteries 226. A second electrode may be located in a subcutaneous subclavical area, such as denoted at 242. Location 242 is remote from the heart 210 and, by way of example may correspond to the position at which an IMD is located. The housing or case of the IMD may be configured to function as an electrode to, among other things, detect impedance and/or sense cardiac activity.

Electrodes at locations 240 and 242 form an extra-cardiac impedance (ECI) vector 244 there between. The electrodes at locations 240 and 242 may be bipolar, mono-polar, tri-polar, or quadra-polar. The ECI vector 244 extends through a substantial portion of the aorta 228, as well as the pulmonary veins and arteries 222 and 226, and other portions of the greater vessels 216. The ECI vector 244 may be referred to as an aorta-centric ECI vector due to the correlation of the vector 244 and the aorta 228. Electrodes at locations 240 and 242 are both outside of the four chambers 230, 232, 234 and 236 of the heart 210.

Optionally, an electrode may be located within a coronary vein that passes along the heart wall, where this electrode is positioned to be outside of, but adjacent to, the left ventricle 234. By way of example, an electrode located in the coronary vein may be positioned at location 246. When an electrode is positioned in the coronary vein proximate to the left ventricle at location 246, a CI vector 248 may be created between electrodes at locations 242 and 246. The CI vector 248 may be referred to as a pulmonary-centric CI vector due to the correlation of the vector 248 and the pulmonary veins and arteries 220 and 224.

Alternatively or in addition, one or more electrodes may be shifted further along the coronary vein to positions proximate locations 250 and configured to operate with an electrode at location 240 at the SVC to form one or more CI vectors 252. The vectors 244, 248 and 252 substantially extend such that impedance variations that are detected along the vectors 244, 252 and 248 correlates closely to changes in the volume of blood flow through the greater vessels 216 and/or one or more chambers. As a further option, a combination of the vectors 244, 248 and 252 may be used to measure impedance. As a further option, alternative CI vectors may be used in place of, or in combination with, the CI vectors 244, 248 and 252.

Impedance measurements detected along CI vectors 244 and 248 closely correlates to cardiac output and the mechanical behavior of the heart. In general, tissue has higher resistance than blood. During systole, blood is injected into the thoracic periphery (which includes the greater vessels). Hence, the tissue of the greater vessels between the extracardiac electrodes (such as at locations 240, 242, 246) becomes engorged with blood. Thus, the impedance along the ECI vectors 244, 248 decreases. During diastole, the amount of blood in the greater vessels decreases. Hence, the impedance along the ECI vectors 244, 248 increases. Impedance measurements along the ECI vectors 244, 248 increase and decrease based upon the amount of blood that is injected into the greater vessels 216.

Figure 3:
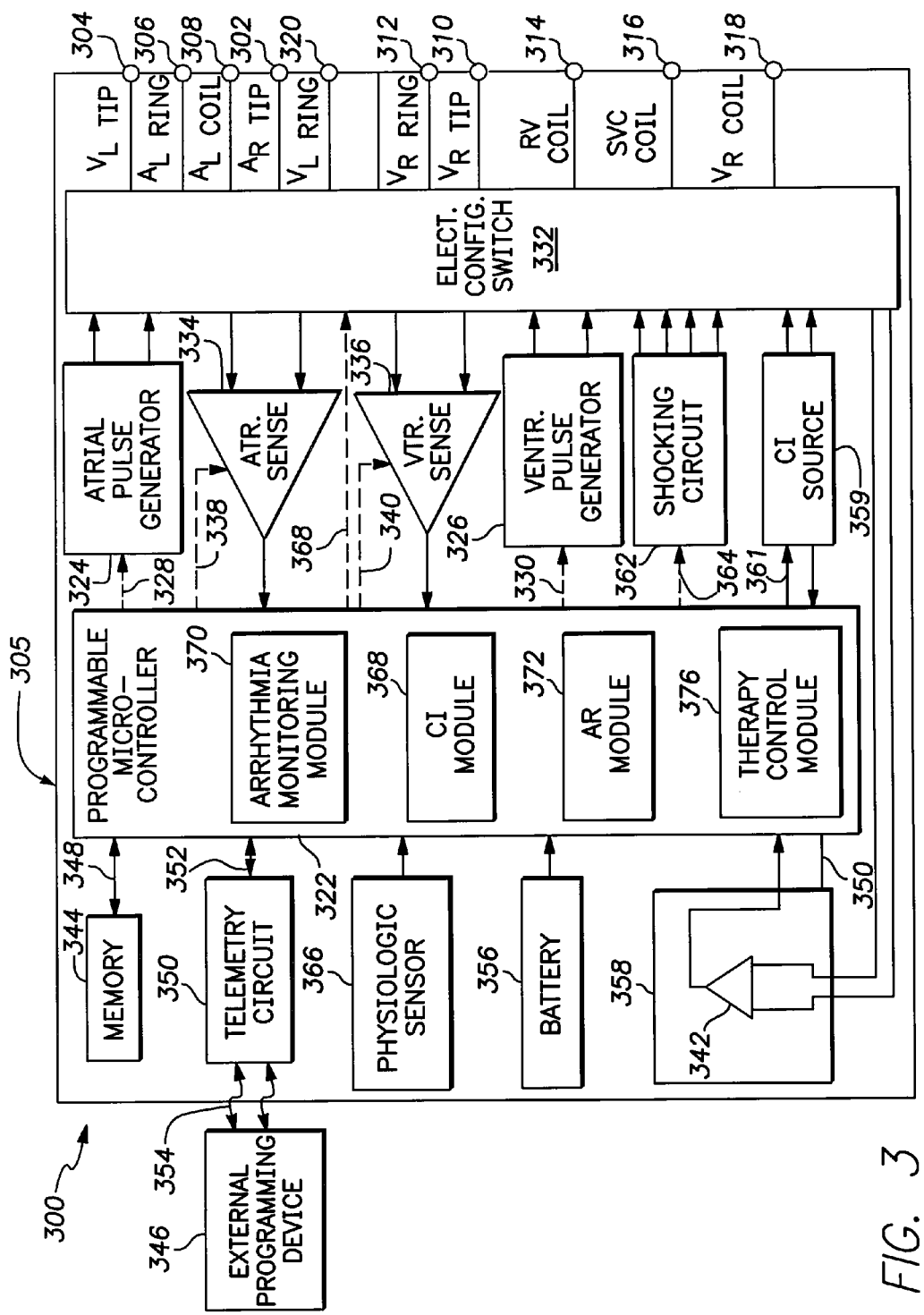
FIG. 3 illustrates a block diagram of exemplary internal components of the IMD in accordance with an alternative embodiment.

FIG. 3 illustrates a block diagram of exemplary internal components of the IMD 100. The IMD 100 is for illustration purposes only, and it is understood that the circuitry could be duplicated, eliminated or disabled in any desired combination to provide a device capable of treating the appropriate chamber(s) of the heart with cardioversion, CRT defibrillation and/or pacing stimulation. The housing 305 for IMD 100 (shown schematically in FIG. 3), is often referred to as the "can", "case" or "case electrode" and may be programmably selected to act as the return electrode for all "unipolar" modes. The housing 305 further includes a connector (not shown) having a plurality of terminals, namely a right atrial tip terminal (AR TIP) 302, a left ventricular tip terminal (VL TIP) 304, a left atrial ring terminal (AL RING) 306, a left atrial shocking terminal (AL COIL) 308, a right ventricular tip terminal (VR TIP) 310, a right ventricular ring terminal (VR RING) 312, a right ventricular shocking terminal (RV COIL) 314, an SVC shocking terminal (SVC COIL) 316, a right ventricular coil terminal (VR COIL) 318 and a left ventricular ring terminal (VL RING) 320.

The IMD 100 includes cardiac impedance (CI) sensing circuitry 358 which is managed by the CI module 368 via a control signal 360. The CI sensor circuitry 358 is configured to be coupled to at least a first combination of the electrodes to sense data associated with cardiac impedance. The CI sensing circuitry 358 is coupled to various combinations of electrodes on one or more of the right atrial lead 116, the coronary sinus lead 118, and the right ventricular lead 114 through the switch 332 to collect impedance data across any combination of desired electrodes 124-138. The CI sensor circuitry 358 collects impedance data by measuring voltage potentials and generating an impedance related voltage measurement stream (also referred to as an impedance data stream) associated with a corresponding CI sensing vector. The CI sensing circuitry 358 is coupled to the switch 332 which connects the CI sensing circuitry 358 so that voltage signals, related to impedance, at any desired electrode may be obtained. The CI sensing circuitry 358, the switch 332 and the electrodes connected thereto define one or more IC sensing channels.

The IMD 100 includes a CI source 359 controlled, by control signal 361, by the CI module 368 to deliver current pulses between one or more electrodes during a predetermined and/or automatically updated sample interval. The current pulses may be bi-phasic, tri-phasic and the like, and separated by a select pulse to pulse interval.

The CI sensing circuitry 358 includes an operational amplifier, configured to operate as a comparator 342, to acquire impedance related voltage signals. The CI sensing circuitry 358 converts the analog signal to a digital signal. Optionally, the inputs to the comparator 342 may represent digitized data that is compared by the comparator 342. The analog or digital voltage data stream is comprised of voltage sample sub-sets spanning over one or more cardiac cycles. The measured voltages and know source current from the IC source 359 are used to calculate actual impedance values for the sample sub-sets and sample sets for one or more cardiac cycles. The impedance data sets are stored in a memory 344 for later processing and/or telemetric transmission to an external device 346. Control signals 360, 361 from the CI module 368 turn the CI sensing circuitry 358 and CI source 359 ON and OFF.

In accordance with an embodiment, the CI sensor circuitry 358 is configured to turn ON and OFF during periodic sample intervals. Each of the sample intervals has an active segment in which a sample sub-set of the impedance data is collected. Each of the sample intervals has an inactive segment in which sample sub-sets are not generated. The therapy module 376 manages a time at which the pacing pulse is delivered to interleave the pacing pulse between active segments of the sample interval. Optionally, the therapy module 376 manages a time at which a coupling capacitor discharges to overlap discharge of the coupling capacitor with the inactive segments of the sample intervals. The coupling capacitor accumulates a coupling charge in connection with delivery of the pacing pulse. The therapy module 376 controls the coupling capacitor to discharge the coupling charge in a separated divided manner over multiple inactive segments of the sample intervals.

The IMD 100 includes a programmable processor module 322, which controls the operation of the IMD 100 based on acquired cardiac signals and collected impedance data. The processor module 322 (also referred to herein as a processor module or unit) typically includes a microprocessor, or equivalent control circuitry, is designed specifically for controlling the delivery of stimulation therapy and may further include RAM or ROM memory, logic and timing circuitry, state machine circuitry, and I/O circuitry. Typically, the processor module 322 includes the ability to process or monitor input signals (e.g., data) as controlled by a program code stored in a memory. Among other things, the processor module 322 receives, processes, and manages storage of digitized data from the various electrodes (shown in FIGS. 1 and 2). The processor module 322 may also analyze the data, for example, in connection with collecting, over a period of time, variations in a segment of interest, CI measurements cardiac output and the like. For example, the processor module 322 monitors variations in one or more of segments of interest such as the ST segment and the R-wave and variations in cardiac output and impedance data.

The modules in the processor module 322 that monitor arrhythmias, CI and CO include a CI module 368, an arrhythmia monitoring module 370, artifact reduction (AR) module 372 and a therapy module 376. The arrhythmia monitoring module 370 determines segment variations such as ST segment variations and changes in the amplitude and rate of the R-wave. The therapy control module 376 assesses and determines what therapy to deliver. The therapy control module 376 is configured to control delivery of pacing pulses in accordance with therapy parameters, therapy timing and based on the cardiac activity sensed.

The therapy module 376 is also configured to control discharge of one or more coupling capacitors electrically connected in series with one or more electrodes that deliver the pacing pulses. In one embodiment, under direction of the AR module 372, the therapy module 376 manages a time at which the coupling capacitor discharges to interleave discharge of the coupling capacitor between active segments (or active CI collection windows) of the sample intervals.

The CI module 368 is configured to manage the CI source 359 to deliver source current and the CI sensor circuitry 358 to collect impedance related voltage measurements during active CI collection windows. In accordance with an embodiment, the CI module 368 is configured to manage the CI sensor circuitry 358 and CI source 359 by turning both ON and OFF during periodic sample intervals. Each of the sample intervals has an active segment in which the CI sensor circuitry 358 and CI source 359 are ON and generate a corresponding sample sub-set of the impedance related voltage measurements. Each of the sample intervals also has an inactive segment in which the CI sensor circuitry 358 and CI source 359 are OFF and do not generate the impedance related voltage measurements. The CI module 368 utilizes the impedance related voltage measurements and the known current delivered by the current CI source 359 to calculate impedance values for each sample. The CI module 368 processes the impedance data collected over at least one cardiac cycle to provide an impedance sample set for the at least one cardiac cycle. The CI module 368 repeats the collection of impedance data for multiple cardiac cycles and may store, transmit or use such data to calculate cardiac output (CO) and/or hemodynamic performance.

In accordance with certain embodiments, the artifact reduction (AR) module 372 is configured manage at least one of i) the therapy timing of the therapy module and ii) the active CI collection windows, to avoid delivery of the pacing pulses during the active CI collection windows in which the CI sensor circuitry collects impedance data. For example, the AR module 372 may be configured to manage the therapy timing to interleave the pacing pulses between the active CI collection windows. Optionally, the AR module 372 may be configured to manage the active CI collection windows by shifting the active CI collection windows relative to the pacing pulses to avoid overlap of the pacing pulses and the active CI collection windows.

In accordance with certain embodiments, the artifact reduction module 372 may also, or alternatively, be configured to identify a reconstruction region in the impedance data and reconstruct a sample sub-set of the impedance data that occurs during the reconstruction region to at least partially remove artifacts in the impedance data associated a pacing pulse. For example, the AR module 372 designates a beginning of the reconstruction region based on a time at which a corresponding pacing pulse is delivered. The reconstruction region has predetermined artifact duration. The reconstruction region may have an artifact duration based on a width of the pacing pulse, a blanking interval following the pacing pulse, and/or a coupling capacitor discharge interval associated with the pacing pulse.

In accordance with an embodiment, the AR module 372 is configured to perform post-collection processing to replace the sample sub-set of the impedance data that occurs during the reconstruction region, with a synthetic sample sub-set by at least one of: A) applying a polynomial fit equation that connects valid sample sub-sets before and after the reconstruction region to bridge the reconstruction region; B) applying interpolation to connect valid sample sub-sets before and after the reconstruction region to bridge the reconstruction region; and C) applying a sinusoidal curve fitting filter to the impedance data before, within and after the reconstruction regions. As part of the generation of the synthetic sample sub-sets, the AR module may be configured to apply at least one of high and low pass filters to the impedance data. The high and/or low pass filters have filter characteristics configured to at least partially correct for artifacts in the sample sub-set collecting while delivering a pacing pulse.

Optionally, the AR module 372 may align the reconstruction regions to overlap in time with at least one of: A) a time at which pacing pulses are delivered in an atrium; B) a time at which pacing pulses are pacing pulses delivered in a ventricle; C) a blanking interval following the pacing pulses; D) a settling time associating with IC sensor; and E) a time at which capacitance is discharged from a coupling capacitor following the pacing pulses.

The IMD 100 includes an atrial pulse generator 324 and a ventricular pulse generator 326 to generate pacing stimulation pulses. In order to provide stimulation therapy in each of the four chambers of the heart, the atrial and ventricular pulse generators 324 and 326, may include dedicated, independent pulse generators, multiplexed pulse generators, or shared pulse generators. The pulse generators, 324 and 326, are controlled by the processor module 322 via appropriate control signals, 328 and 330, respectively, to trigger or inhibit the stimulation pulses.

Switch 332 includes a plurality of switches for connecting the desired electrodes, including the electrodes 104, 124 through 138, and 240, 244, 246 to the appropriate I/O circuits, thereby providing complete electrode programmability. The switch 332, in response to a control signal 367 from the processor module 322, determines the polarity of stimulation pulses (e.g., unipolar, bipolar, etc.) by selectively closing the appropriate combination of switches (not shown) as is known in the art. Atrial sensing circuits 334 and ventricular sensing circuits 336 may also be selectively coupled to the leads 114, 116 and 118 through the switch 332 for detecting the presence of cardiac activity in each of the four chambers of the heart 102. Control signals 338 and 340 from processor module 322 direct output of the atrial and ventricular sensing circuits 334 and 336 that are connected to the processor module 322. In this manner, the atrial and ventricular sensing circuits 334 and 336 are able to trigger or inhibit the atrial and ventricular pulse generators 324 and 326.

The processor module 322 is coupled to memory 344 by a suitable data/address bus 348, wherein the programmable operating parameters used by the processor module 322 are stored and modified, as required, in order to customize the operation of IMD 100 to suit the needs of a particular patient. The memory 344 may also store data indicative of myocardial function, such as the IEGM data, ST segment shifts, reference ST segment shifts, ST segment shift thresholds, R wave amplitudes, R wave amplitude changes, impedance vectors, trend information associated with ischemic episodes, and the like for a desired period of time (e.g., 6 hours, 12 hours, 18 hours or 24 hours, and the like). The memory 344 stores impedance data streams and therapy timing and therapy parameters (e.g., at least one of AV delay, V-V delay, stimulation rate, stimulating electrodes chosen for actuating pacing, and stimulation lead configuration).

The operating parameters of the IMD 100 may be non-invasively programmed into the memory 344 through a telemetry circuit 350 in communication with the external device 346, such as an external device 346, a trans-telephonic transceiver or a diagnostic system analyzer. The telemetry circuit 350 is activated by the processor module 322 by a control signal 352. The telemetry circuit 350 allows intra-cardiac electrograms, impedance data and status information relating to the operation of IMD 100 (as contained in the processor module 322 or memory 344), to be sent to the external device 346 through an established communication link 354. The IMD 100 additionally includes the battery 356, which provides operating power to all of the circuits shown within the housing 305, including the processor module 322. The IMD 100 also includes a physiologic sensor 366 that may be used to adjust pacing stimulation rate according to the exercise state of the patient.

In the case where IMD 100 is intended to operate as an ICD device, the IMD 100 detects the occurrence of an arrhythmia, confirms insufficient CO and automatically applies an appropriate electrical shock therapy to the heart aimed at terminating the detected arrhythmia. To this end, the processor module 322 further controls a shocking circuit 362 by way of a control signal 364. The shocking circuit 362 generates shocking pulses of low (up to 0.5 joules), moderate (0.5-10 joules) or high energy (11 to 40 joules). Such shocking pulses are applied to the heart 102 (shown in FIG. 1) of the patient through at least two shocking electrodes, and as shown in this embodiment, selected from the left atrial coil electrode 128 (shown in FIG. 1), the RV coil electrode 134 (shown in FIG. 1), and/or the SVC coil electrode 138 (shown in FIG. 1). When the IMD operates as a pacemaker, the processor module applies a therapy using cardiac pacing conditions associated with the preferred hemodynamic performance based on the CI measurements. The processor module compares the CI measurements to determine a preferred hemodynamic performance based on the CI measurements. The processor module applies a therapy using cardiac pacing conditions associated with the preferred hemodynamic performance based on the stored CI measurements.

Figure 4:
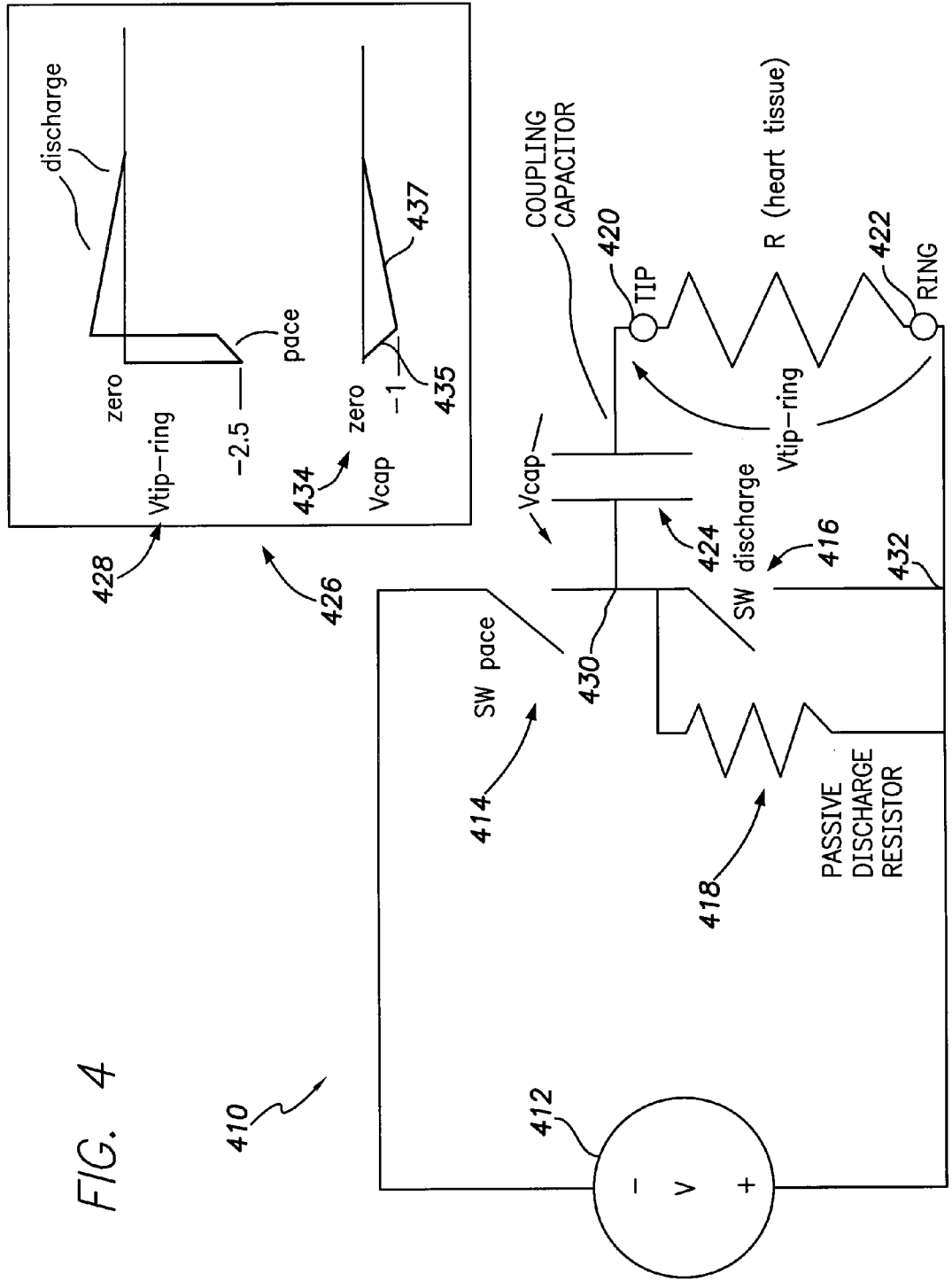
FIG. 4 illustrates a schematic representation of a pacing circuit within the IMD in accordance with an alternative embodiment.

FIG. 4 illustrates a schematic representation of a pacing circuit within the IMD 100. The pacing circuit 410 includes a power supply 412 that is connected in series with a pacing switch 414 and a discharge switch 416. A node 430, between the pacing switch 414 and discharge switch 416, is connected to an electrode, such as a tip electrode 420 that is provided at a desired stimulus site proximate to the heart (generally denoted at R). Node 432 on an opposite side of the discharge switch 416 is coupled to the power supply 412 and to a second electrode, such as a ring electrode 422 that is also located at a desired stimulus site proximate to the heart R. During a pacing operation, pacing switch 414 is closed, while discharge switch 416 is held open, such that a pacing stimulus is delivered from the power supply 412 to the tip and ring electrodes 420 and 422, thereby inducing a tip to ring voltage differential between the tip and ring electrodes 420 and 422 sufficient to achieve capture. When the pacing operation is completed, the pacing switch 414 opens.

A coupling capacitor 424 is provided between the node 430 and the tip electrode 420. A passive discharge resistor 418 is also provided between nodes 430 and node 432, in parallel with the discharge switch 416. In general, the coupling capacitor 424 is provided to separate the power supply stage of the pacing circuit 410 from the electrode stage (generally including the tip and ring electrodes 420 and 422). In general, the coupling capacitor 424 is used to filter noise and undesirable signals from passing between the power supply 412 and the tip electrode 420.

FIG. 4 also illustrates an exemplary change graph 426 showing the charge accumulation and discharge over time exhibited across the tip and ring electrodes 420 and 422 (as denoted at the V tip-ring discharge signal 428) and the charge accumulation across the coupling capacitor 424 (as denoted in the Vcap potential charge graph 434). During operation, initially, the coupling capacitor 424 holds a zero charge potential. To perform a pacing operation, the pacing switch 414 is closed. The coupling capacitor 424 instantaneously becomes a short circuit that couples the negative voltage –V from the power supply 412 to the tip electrode 420. The coupling capacitor 424 then begins to build up charge thereon which is illustrated as a negative potential increase 435 in the example of FIG. 4 (given that the coupling capacitor 424 is connected to the negative potential –V of power supply 412). As one example, the coupling capacitor may store up to a potential of approximately 0.2×V, where V corresponds to the voltage potential across the power supply 412. In this example, if the power supply 412 provides a 2.5 volt differential, then the coupling capacitor 424 will charge to approximately –0.5 volts by the end of a pacing operation.

The pacing switch 414 then switches open at the end of the pacing operation. At this point, the coupling capacitor 424 has a negative potential stored thereon (e.g., –0.5 volts). Next, the coupling capacitor 424 is discharged to remove the negative charge accumulated thereon (generally referred to as "active discharge"). The coupling capacitor 424 is actively discharged by closing the discharge switch 416, thereby dumping the charge from the coupling capacitor 424 through the heart R between tip and ring electrodes 420 and 422. It should be recognized that the amount of charge held in the coupling capacitor 424, when discharged through the heart R, is significantly below the levels needed to achieve capture of the heart. Thus, the discharge operation (which is also performed during the time period when the heart is in a refractory state) does not interfere with the normal physiologic behavior sought to be achieved through the pacing operation. The discharge switch 416 is held in a shut position for a predetermined period of time while discharging at 437 and then opened to complete the active discharge operation.

In the event that the active discharge operations does not completely remove all charge from the coupling capacitor 424, any remaining charge held by the coupling capacitor 424 is discharged through the passive discharge resistor 418. As one example, the passive discharge resistor 418 may be between 30,000-50,000 ohms of resistance and is utilized to remove or clean up any remaining charge on the coupling capacitor 424.

Figure 5:
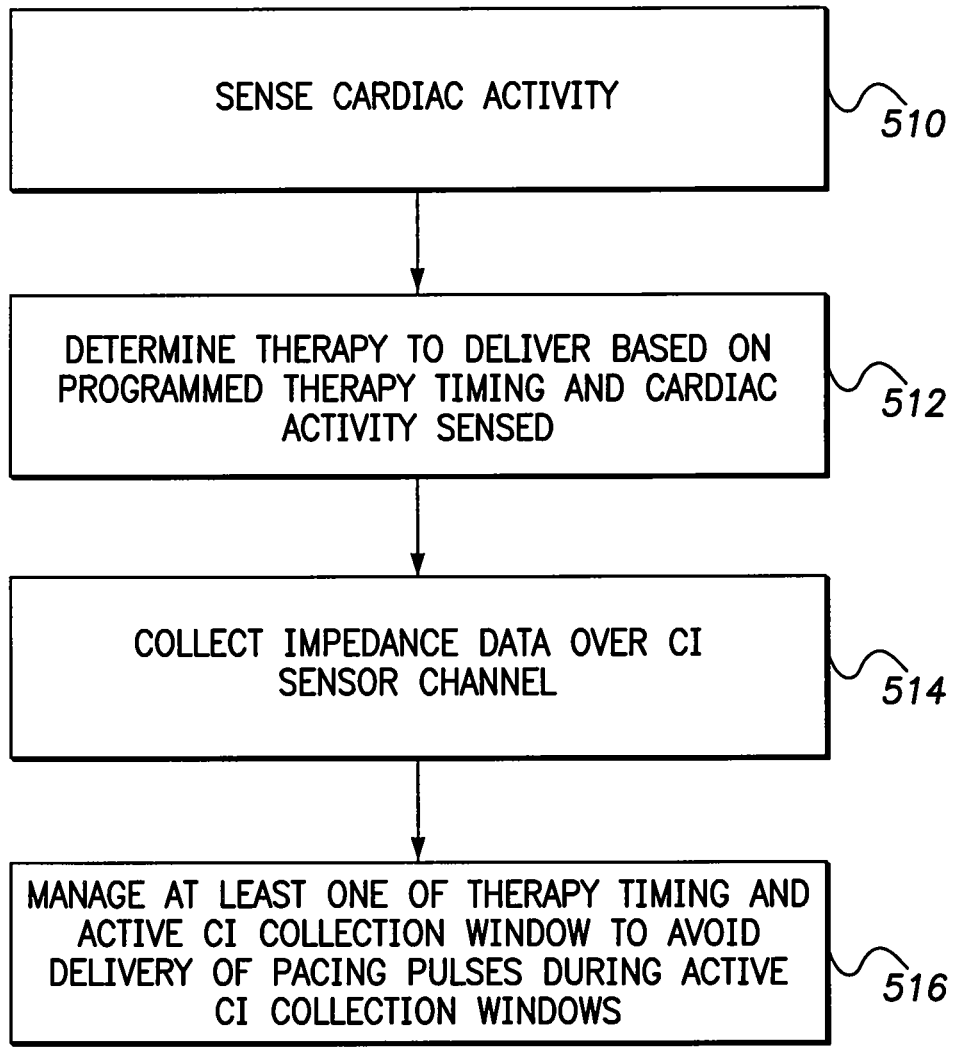
FIG. 5 illustrates a processing sequence performed in accordance with at least one embodiment for improving impedance data quality in the presence of pacing pulses in accordance with an alternative embodiment.

FIG. 5 illustrates a processing sequence performed in accordance with at least one embodiment for improving impedance data quality in the presence of pacing pulses. Beginning at 510, the IMD 100 senses cardiac activity in accordance with a normal sensing operation from one or more electrodes, or for one or more combinations of electrodes.

At 512, the process determines a therapy to be delivered (if any) based on programmed therapy timing, as well as the cardiac activity sensed at 510. The programmed therapy timing includes the pacing parameters, as well as other parameters that may be programmed by the physician, at time of manufacture and/or automatically updated during operation of the IMD 100. As one example, when performing DDD mode pacing, the sensed cardiac activity at 510 may include an intrinsic or paced atrial event, but without a corresponding intrinsic ventricular event. In this example, at 512, the process would determine that a ventricular paced event should be delivered in one or both ventricles in accordance with program AV timing.

At 514, the process collects impedance data over one or more CI sensor channels. As explained herein, one or more CI sensing vectors may be defined between select combinations of electrodes. Voltage measurements are taken and impedance data is collected in connection with each CI sensing vector. The CI sensor circuitry 358 associated with the CI sensor channel measure voltages and the CI module 368 generates an impedance data stream (from measured voltage and source current) associated with the CI sensing vector.

At 516, the process manages the CI sensor channel to collect the impedance data only during active CI collection windows. In accordance with at least one embodiment, the managing operations 516 includes performing artifact reduction by managing at least one of the therapy timing and the active CI collection windows to avoid delivering pacing pulses during the active CI collection windows during which the CI collector channel collects impedance data.

The managing operation 516 is explained further below in connection with FIG. 6.

Figure 6:
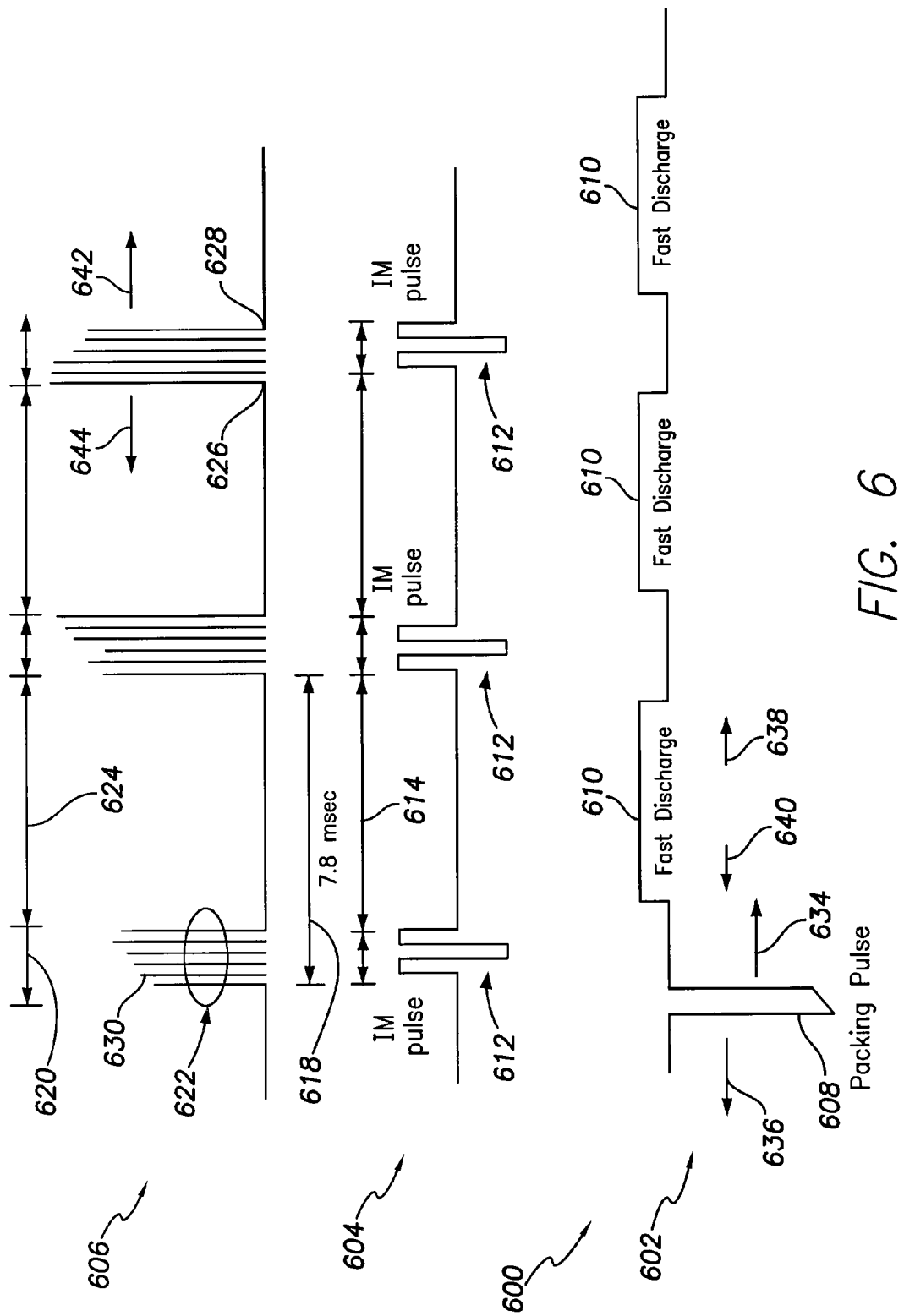
FIG. 6 illustrates exemplary timing diagrams associated with delivering a pacing pulse and collecting impedance data in accordance with an alternative embodiment.

FIG. 6 illustrates exemplary timing diagrams associated with delivering a pacing pulse and collecting impedance data. The timing diagrams 600 in FIG. 6 include a pacing channel 602, a CI source channel 604 a CI sensor channel 606. Within the pacing channel 602, a pacing pulse 608 or pulse train is delivered followed by discharge of the potential that has built up in the coupling capacitor, during one or more fast full or partial discharge segments 610.

The partial discharge segments 610 in FIG. 6 cumulatively correspond to charge build-up associated with a single pacing pulse 608 or pulse train. The number of partial discharge segments 610 will vary based on the charge stored on the coupling capacitor, the rate at which the coupling capacitor may be discharged and the duration of each discharge segment 610.

The CI source channel 604 includes one or a series of current pulses 612 that are delivered at a predefined pulse-to-pulse spacing 614. The current pulses 612 are delivered between predetermined combinations of electrodes that operate as current sources in connection with collection of impedance data. As one example, the current pulses 612 may be mono-phasic, bi-phasic or tri-phasic. In the example of FIG. 6, the current pulses 612 are tri-phasic. The current pulses 612 are delivered periodically based on a sample interval 618. The current pulses 612 have a predetermined pulse width 613 with a predetermined pulse spacing 614 there between.

The CI sensor channel 606 is managed to overlap with the current pulses 612. The CI sensor channel 606 utilizes the same sample interval 618 as the current pulses 612. The CI sensor channel 606 includes, within each sample interval 618, an active segment 620 and an inactive segment 624. During the active segment 620 (temporally aligning with the pulse width 613), an active CI collection window 622 is open. When the active CI collection window 622 is opened, at least one individual sample 630 is collected. A sample subset 632, of at least one sample 630, is collected during an individual active CI collection window. Optionally, when more than one sample 630 is collected in a single CI collection window 622, the samples 630 may be combined (e.g., averaged, summed, median, mean). A separate sample subset 632 (of at least one sample 630) is collected during each sample interval 618 over one or more cardiac cycles. The sample subsets 632 collectively form a sample set for the entire cardiac cycle.

The active CI collection windows 622 are turned ON and OFF at points 626 and 628, respectively to start and stop collection of the individual sample 630. The sample(s) within the subsets 632 over one or more cardiac cycles generally form the impedance data collected at 514 (FIG. 5).

Returning to FIG. 5, the managing operation at 516 turns the CI sensor channel ON and OFF (points 626 and 628) during the periodic sample intervals 618. Each of the sample intervals 618 has an active segment 620 in which the CI sensor channel is ON and generates a corresponding sample subset 632 of one or more impedance data values. Each of the sample intervals 618 also includes an inactive segment 624 in which the CI sensor channel 606 is OFF and does not generate impedance data. The impedance data is collected over at least one cardiac cycle and is processed to provide an impedance sample set for the associated one or more cardiac cycles.

The managing operation at 516 also controls a time at which the pacing pulse 608 is delivered as well as a time at which the coupling capacitor is discharged during the fast discharge segments 610. In one example, the AR managing operation 516 may shift the pacing pulse forward or backward in time a few milliseconds, as denoted by arrows 634 and 636 to cause the pacing pulse 608 to be interleaved between the active segments 620 of the impedance sampling interval 618. By shifting the pacing pulse 608 forward or backward 634, 636, the artifact reduction operation 516 manages the therapy timing to interleave the pacing pulse 608 between the active CI collection windows 622. The artifact reduction managing operation 516 may shift the fast discharge segments 610 forward or backward as denoted at arrows 638 and 640 in order to interleave discharge of the coupling capacitor between the active segments 620 (corresponding to the active CI windows 622) in the sampling interval 618. In the foregoing manner, the pacing pulses 508 and fast discharge segments 610 occur during the inactive segments 624.

The AR managing operation 516 may cause the coupling capacitor to discharge entirely in one segment, or alternatively cause the coupling capacitor to split or divide the discharge operation into multiple partial discharge segments 610. When divided, the coupling capacitor will discharge only a portion of the coupling charge in each inactive segment 624, corresponding to split or partial discharge segments 610.

Optionally, in addition to (or instead of) shifting the pacing pulse 608 and fast discharge segment 610, the artifact reduction managing operation 516 may also manage the active CI collection windows 622 by shifting the active CI collection windows 622 forward or backward (as denoted at arrows 642 and 644) to avoid overlap of the pacing pulse 608, fast discharge segments 610 and the active CI collection windows 622. The AR operation may shift the active CI collection windows 622 by changing the length of the inactive segments 624 within a select subset of the sample intervals 618. Alternatively, the AR operation may adjust the length of one or more inactive segments 624 to permanently shift the sampling interval forward or backward in time 642, 644 to avoid overlap with the pacing operations. As a further option, the AR operation may manage the CI sensor channel 606 by skipping one or more CI active collection windows such as when an individual pacing pulse 608 would otherwise overlap with the active CI collection window.

Optionally, the AR management operation may also manage a fast recharge operation for the charge storage device used to deliver therapy. In the event that the fast recharge operation is found to introduce artifacts into the impedance data, the AR management operation may cause the fast recharge to be interleaved between the active IC collection windows in the same manner as coupling capacitor discharge segments and pacing pulses.

Figure 7:
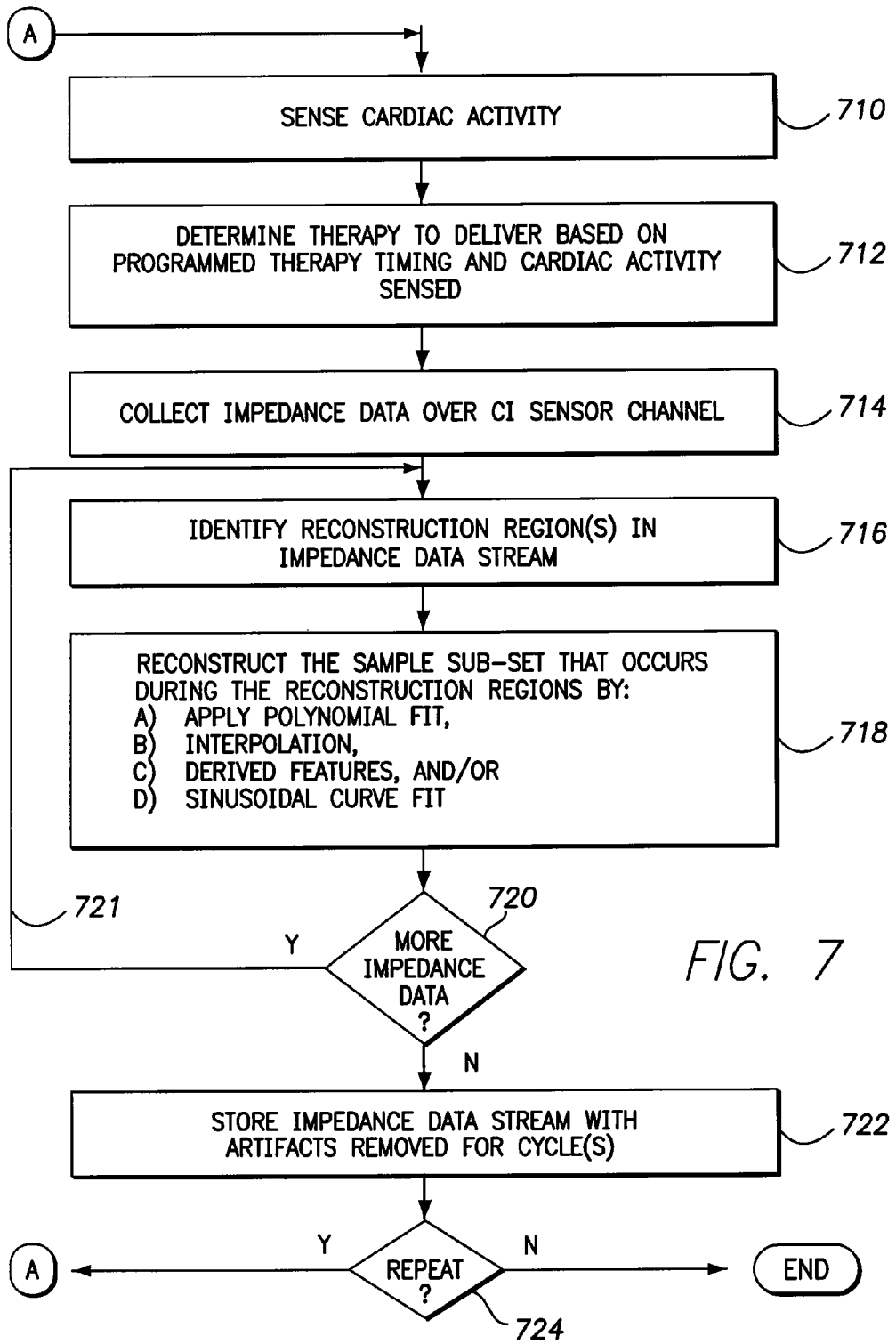
FIG. 7 illustrates a processing sequence performed in accordance with at least one embodiment for removing artifacts from impedance data post-collection.

FIG. 7 illustrates a processing sequence performed in accordance with at least one embodiment for removing artifacts from impedance data post-collection. Beginning at 710, the IMD 100 senses cardiac activity in accordance with a sensing operation from one or more electrodes or from one or more combinations of electrodes. At 712, the process determines whether a therapy should be delivered (and the type of therapy) based on programmed therapy timing parameters and based on the cardiac activity sensed at 710. The programmed therapy timing parameters may be programmed by a physician, at the time that the IMD 100 is manufactured and/or automatically updated during operation of the IMD 100.

At 714, the process collects impedance data over one or more CI sensor channels. The operations at 710-714 may be performed for a portion of a cardiac cycle, over a complete cardiac cycle, or over multiple cardiac cycles. The operations at 710-714 may be performed simultaneously, in parallel and/or in series. Cardiac activity and impedance data are continuously sensed during each cardiac cycle.

As one example, the cardiac activity may be measured as voltage potentials between two or more electrodes. The voltage potentials may represent intrinsic or paced events, as well as coupling capacitor discharge events. The collection of impedance data may also utilize measurement of voltage potentials between two or more electrodes while a current source is applied between the same or different electrodes.

The timing associated with collection of impedance data may be the same as or differ from the sampling in intervals discussed above in connection with FIGS. 5-6. For example, the collection operation at 714 may perform voltage measurements at a sampling interval of every 7.5 msec., 10 msec., 20 msec., and the like. During each sampling interval, the active CI collection window may be a few milliseconds, microseconds and the like, followed by an inactive segment. During each active CI collection window, one or more voltage measurements may be measured and one or more current source pulses may be applied.

Figure 8:
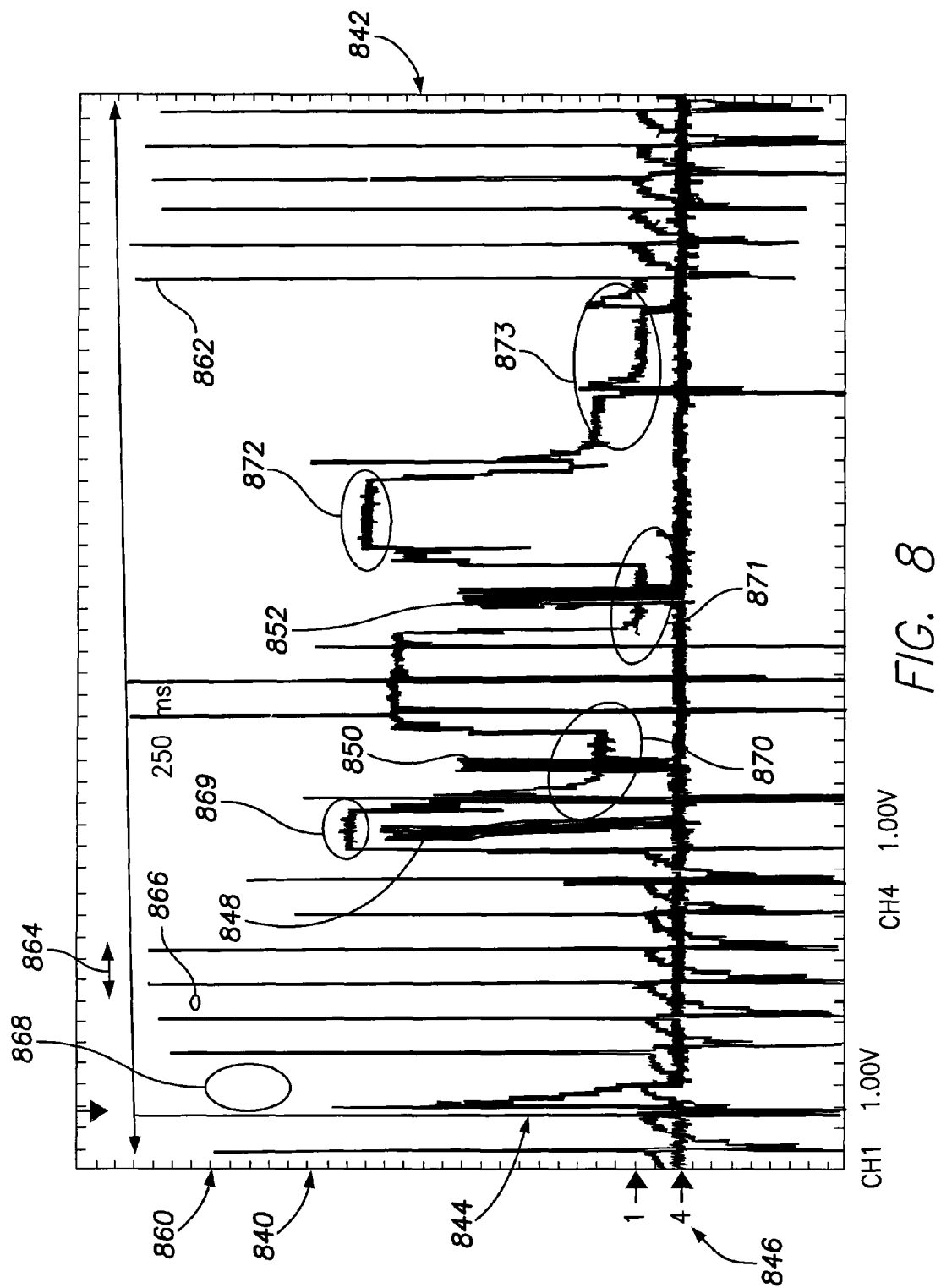
FIG. 8 illustrates an exemplary recording of impedance related voltage measurements, while in the presence of delivering atrial and ventricular pacing pulses in accordance with an alternative embodiment.

Attention is directed to FIG. 8, which illustrates an exemplary recording of impedance related voltage measurements, while in the presence of delivering atrial and ventricular pacing pulses. In FIG. 8, the horizontal axis corresponds to time, while two separate vertical axes are being utilized, namely one in connection with impedance related voltage measurements 840 and one in connection with pacing pulses (as denoted by voltage scale 842). FIG. 8 illustrates a therapy channel 846 that is representative of an example of therapy that may be delivered. In the therapy example of FIG. 8, an atrial paced event 844 is delivered at a desired point in time, relative to the sensed cardiac activity, followed by a collection of ventricular paced events, namely an LV1 paced event 848, an LV2 paced event 850 and an RV paced event 852. In the example of FIG. 8, the IMD is configured to provide multipoint pacing (MPP) in which one or more paced events are delivered in one or both atrium, and if necessary followed by one or more paced events in one or both ventricles. In the example of FIG. 8, the IMD delivered a series of paced events in the LV, followed by a paced event in the RV.

FIG. 8 also illustrates impedance related voltage measurements 860 generally represented as a series of voltage spikes of varying height. The impedance related voltage measurements 860 are comprised of sample subsets 862 (each of which includes one or more data values or samples, but is denoted by a single spike in FIG. 8). The sample subsets 862 are collected at a predetermined sample interval 864 corresponding to the active CI collection windows and separated by inactive segments. The inactive segment width is noted at 866. The height differences in the sample sub-sets 862 represent differences in the measured voltages.

In the method of FIGS. 7-10, the timing of the atrial and ventricular paced events 844, 848, 850, 852 are not shifted or otherwise managed to avoid overlap with sample subsets 862 within the impedance related voltage measurements 860. Instead, the atrial and ventricular paced events 844, 848-852 are delivered primarily based upon programmed therapy timing parameters. Hence, as explained above, the potential exists that the atrial and/or ventricular paced events may occur during active CI collection windows and thus introduce artifacts into the impedance related voltage measurements 860. In the example of FIG. 8, artifacts exist. An atrial paced event 844 occurs at a time that causes a next successive sample subset of the impedance related voltage measurements 860 to not be measured as illustrated in the void area 868. The LV1 paced event 848 causes an artifact 869 in the impedance related voltage measurements 860. The LV2 paced event 850 and the RV paced event 852 similarly cause artifacts 870 and 871, respectively, to occur in the impedance data stream 860.

As also illustrated in FIG. 8, artifacts 872 and 873 are created during the times at which the pacing system causes fast discharge of the coupling capacitor. The void 868 represents one type of artifact manifestation, namely a "missed" or "blank" impedance sample sub-set. The high, medium or low noise signals in the areas denoted as artifacts 869-873 represent other types of artifact manifestations. Hence, a series of artifacts 868-873 are introduced into the impedance related voltage measurements 860 in connection with atrial and ventricular paced events 844-852 and coupling capacitor discharge events (not separately illustrated). The voltage measurements 860 and the current source signals are used to calculate the impedance data stream at 714 (FIG. 7).

Returning to FIG. 7, the process of FIG. 7 is configured to correct for the artifacts created due to paced events and fast coupling capacitor discharge events. At 716, the process identifies reconstruction regions, within the impedance data stream, for which impedance data has been (potentially) corrupted by artifacts caused by paced events or fast discharge operations. As one example, the identification operation 716 may define artifact correction windows that are established relative to each paced or discharge event. For example, an artifact correction window may be set to begin at the beginning or end of a paced event and continue for a predetermined or automatically determined period of time following the start or end of the paced event. Similarly, the artifact correction windows may be set to begin at the same time or slightly before the beginning of a fast discharge operation. The length of the artifact correction window associated with a paced event or fast discharge event may be preprogrammed or alternatively calculated by the IMD during operation. Optionally, the artifact correction windows may be set to begin a predetermined offset amount of time before the beginning of a paced event or fast discharge event.

At 716, the artifact reduction operation may designate the reconstruction regions, in one example, to begin based on a time at which a corresponding pacing pulse is delivered, with the reconstruction region being given a predetermined artifact duration. As an example, the reconstruction regions may be afforded artifact durations based on the width of the pacing pulse, based on a blanking interval following a pacing pulse, based on a coupling capacitor discharge interval associated with the pacing pulse and the like.

In 716, the identifying operation may align the reconstruction region to overlap in time with at least one of: A) a time at which pacing pulses are delivered in an atrium (e.g., RA or LA); B) a time at which pacing pulses are delivered in a ventricle (e.g., RV and/or LV); C) a blanking interval following one or more pacing pulses; D) a settling time associated with the IC sensor circuitry and channel; and E) a time at which capacitance is discharged from a coupling capacitor following on or more pacing pulses.

At 718, the process reconstructs the sample subset or sample subsets that occur during the reconstruction region or reconstruction regions based upon one or more reconstruction techniques. As examples, the reconstruction techniques may include one or more of applying a polynomial fit equation to the impedance data within the reconstruction regions to form one or more "synthetic" (e.g., mathematically calculated) sample subsets that remove artifacts. As a further example, the polynomial fit equation may utilize, not only to impedance data occurring during the reconstruction region, but may also utilize impedance data occurring before and/or after the reconstruction region to derive synthetic sample subsets. As another example, reconstruction may be performed based on an interpolation operation whereby sample subsets are analyzed before and after the reconstruction region and a synthetic sample subset is created by interpolating between the select valid sample subsets occurring before and after the reconstruction region.

As a further example, reconstruction may be performed based upon features that are derived from the impedance data stream and/or features derived from the cardiac signal. As another example, reconstruction may be performed utilizing a curve fitting algorithm, such as a sinusoidal curve fitting algorithm and the like. The curve fitting algorithm may represent a sinusoidal curve fitting filter that is applied to the impedance data before, within and after the associated reconstruction regions.

Optionally, the reconstruction technique may utilize filtering, such as applying at least one high pass and/or low pass filter to the impedance data. The high and low pass filters may be provided with filter characteristics that are configured to at least partially correct for the artifacts while delivering pacing pulses. Alternatively, the high and/or low filters may be applied in combination with, or as the only form of reconstruction, to remove artifacts from the impedance data, with or without utilizing a polynomial fit equation, interpolation, derive features or a sinusoidal curve fitting filter.

Optionally, the reconstruction techniques may be applied to multiple cardiac cycles, such that impedance collected over multiple cardiac cycles are utilized in combination to correct for artifacts within the reconstruction regions.

Figure 9:
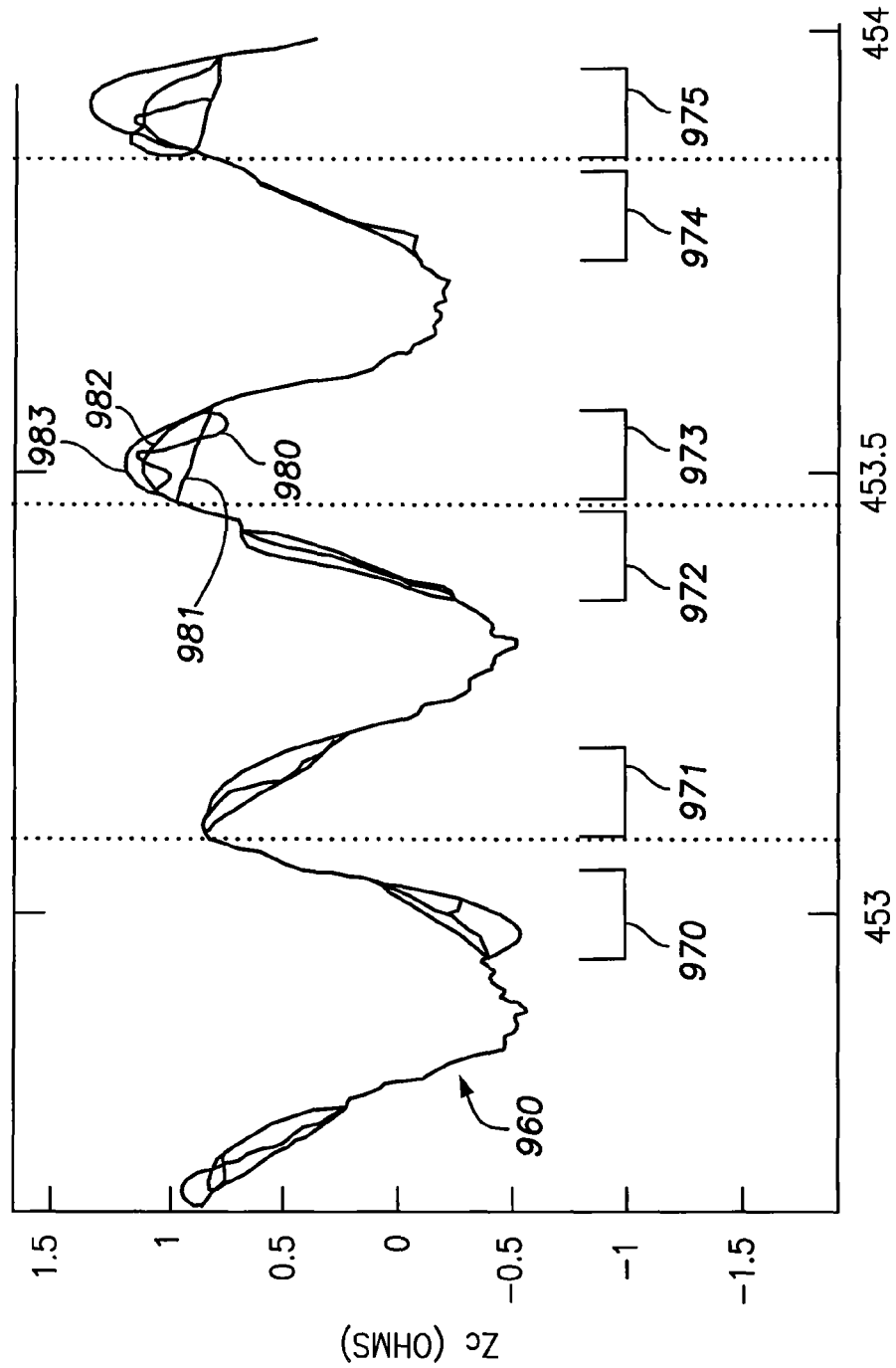
FIG. 9 illustrates an exemplary impedance data stream calculated at (based on voltage measurements) in accordance with an embodiment in the presences of paced and discharge events in accordance with an alternative embodiment.

FIG. 9 illustrates an exemplary impedance data stream 960 calculated at 714 (based on voltage measurements) in accordance with an embodiment in the presences of paced and discharge events. The impedance data stream 960 is illustrated with time as the horizontal axis and with impedance as the vertical axis. Along the vertical axis, an impedance of zero ohms is shown as a central point, with the dynamic range of the impedance varying between 1.5 ohms and −1.5 ohms. In FIG. 9, the impedance data stream 960 is shown for three cardiac cycles. Within the impedance data stream 960, the original data stream is overlaid with multiple alternative synthetic sample subsets within the reconstruction regions.

In accordance with the operation at 716 (FIG. 7), reconstructions regions 970-975 are identified, based upon paced and fast discharge events occurring in connection with the therapy. The reconstruction regions generally align in time with portions of the impedance data stream 960 that do or potentially may include artifacts. With respect to the reconstruction region 973, the original sample subsets of impedance data are denoted by segment 980. Segment 980 includes artifacts, such as caused by an atrial or ventricular paced event. A single pacing pulse may affect one or more samples of the impedance data. Further, multiple pacing pulses may effect a single sample of the impedance data. This will depend in part on the AV interval, blanking interval, filtering and the like. Within the reconstruction region 973, synthetic sample subsets have been created in an effort to reconstruct the expected or true shape of the impedance data stream, when the artifacts are removed.

In FIG. 9, three alternative reconstructions processes have been applied to form three alternative synthetic sample subsets. The segment 981 corresponds to a linear mathematic model, while segment 982 corresponds to a spline type mathematic model, while segment 983 corresponds to a polynomial mathematic model. As one example, the linear mathematic model may simply draw a relatively straight line between, the impedance data values at the beginning and the end of the reconstruction region 973. The spline and polynomial mathematic models may apply alternative equations to the impedance data before, during and after the reconstruction region 973 in order to estimate the values of the impedance data when the artifacts are removed. In FIG. 9, exemplary segments are illustrated in each of the reconstruction regions 970-975 that may occur when applying the examples of mathematical models for linear, polynomial and spline type calculations.

Returning to FIG. 7, once the sampling subsets have been reconstructed at 718, flow moves to 720 where it is determined whether more impedance data has been collected that needs to be corrected. If yes, flow returns along path 721 at which additional reconstruction regions are identified at 716 and sample subsets are reconstructed at 718. When at 720, it is determined that no more impedance data exists to be corrected, flow moves to 722 where the impedance data stream with the removed artifacts (or "artifact-free" data) is stored in memory. Again, the impedance data stream stored at 722 may correspond to a single cardiac cycle, multiple cardiac cycles, an average of multiple cardiac cycles and the like. Next, at 724 it is determined whether the process should be repeated. When the process is to be repeated, flow returns to the top of FIG. 7, otherwise the process ends.

Figure 10:
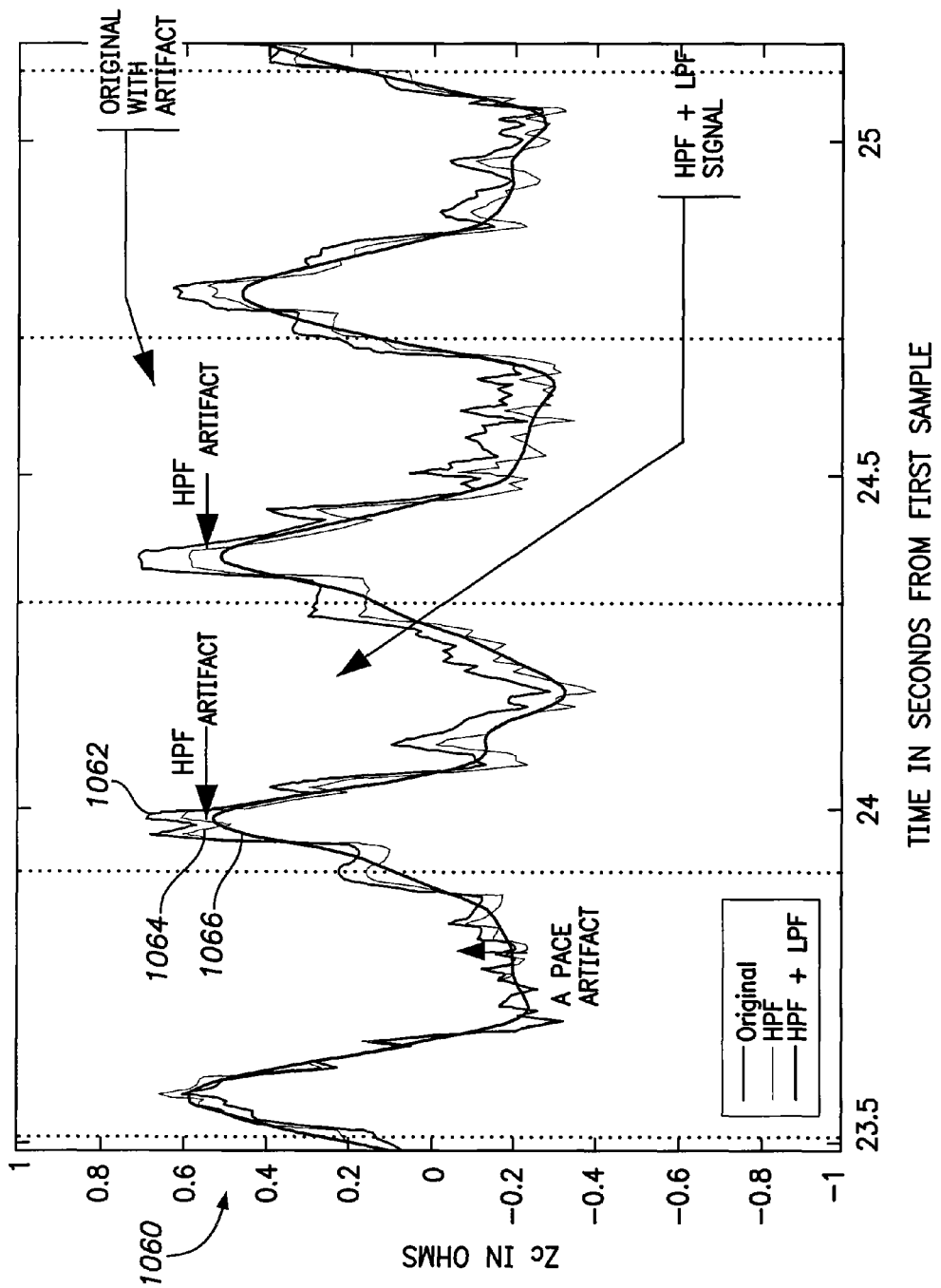
FIG. 10 illustrates an impedance data stream that is collected over multiple cardiac cycles during the presence of pacing and discharge events and processed using high and low pass filters in accordance with an alternative embodiment.

FIG. 10 illustrates an impedance data stream 1060 that is collected over multiple cardiac cycles during the presence of pacing and discharge events and processed using high and low pass filters. The impedance data stream illustrated in FIG. 10 represent an original impedance data stream with artifacts (as denoted at 1062, an impedance data stream to which a high pass filter has been applied as denoted at 1064, and an impedance data stream in which both a high pass filter and a low pass filter have been applied to the data stream as denoted at 1066. The high pass and low pass filters utilized in connection with the impedance data stream of FIG. 10 may be applied to all of the impedance data collected over the multiple cardiac cycles. Optionally, and alternatively, the high and/or low impedance filters may be applied only to the sample subsets within the impedance data stream occurring during reconstruction regions (identified as explained above).

Figure 11:
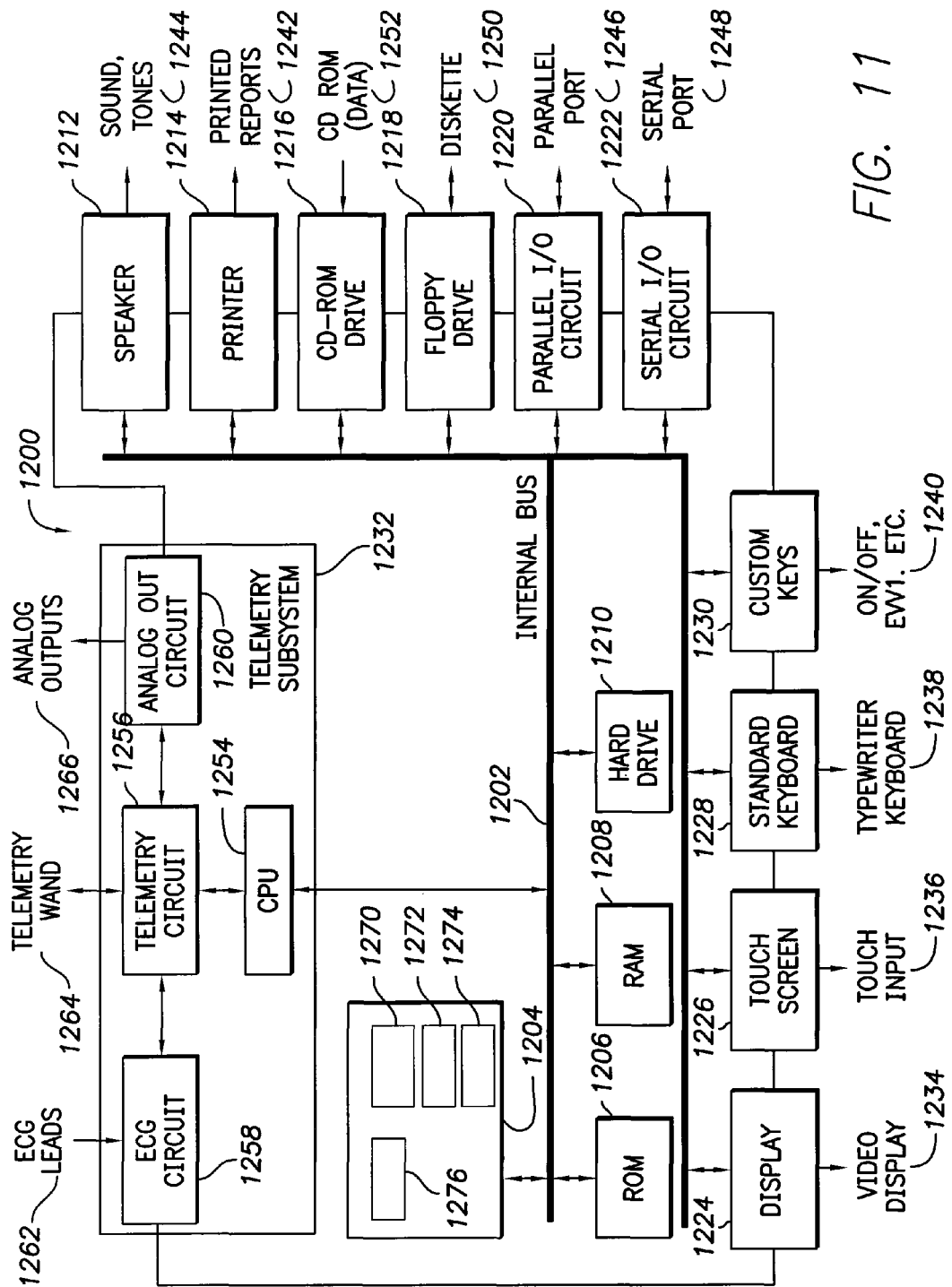
FIG. 11 illustrates a functional block diagram of the external device, such as a programmer that is operated by a physician, a health care worker, or a patient to interface with IMD in accordance with an alternative embodiment.

FIG. 11 illustrates a functional block diagram of the external device 1200, such as a programmer that is operated by a physician, a health care worker, or a patient to interface with IMD 100. The external device 1200 may be utilized in a hospital setting, a physician's office, or even the patient's home to communicate with the IMD 1200 to change a variety of operational parameters regarding the therapy provided by the IMD 100 as well as to select among physiological parameters to be monitored and recorded by the IMD 100. For example, the external device 1200 may be used to program coronary episode related parameters, such as ECI values, ECI templates, ECI thresholds, CO thresholds, and the like. Further, the external device 1200 may be utilized to interrogate the IMD 100 to determine the condition of a patient, to adjust the physiological parameters monitored or to adapt the therapy to a more efficacious one in a non-invasive manner. Further, the external device 300 may represent an external PSA used during implant of an IMD. The external device 1200, when used as a PSA during implant of an IMD, is in accordance with the intraoperative procedures described herein. The PSA would be connected to leads as described herein to delivery therapies. The external device 1200 may include all of the connections, switch network, sensors, generators, arrhythmia detection, ECI measurement, CO assessment and therapy delivery capabilities of an IMD such as in FIG. 3.

External device 1200 includes an internal bus 1202 that connects/interfaces with a processor module 1204, ROM 1206, RAM 1208, a hard drive 1210, a speaker 1212, a printer 1214, a CD-ROM drive 1216, a floppy drive 1218, a parallel I/O circuit 1220, a serial I/O circuit 1222, the display 1224, a touch screen 1226, a standard keyboard connection 1228, custom keys 1230, and a telemetry subsystem 1232. The internal bus 1202 is an address/data bus that transfers information (e.g., either memory data or a memory address from which data will be either stored or retrieved) between the various components described. The hard drive 1210 may store operational programs as well as data, such as reference ST segments, ST thresholds, impedance thresholds, other thresholds, timing information and the like.

The CPU 1204 typically includes a microprocessor, a micro-controller, or equivalent control circuitry, designed specifically to control interfacing with the external device 1200 and with the IMD 100 (shown in FIG. 10). The CPU 1204 may further include RAM or ROM memory, logic and timing circuitry, state machine circuitry, and I/O circuitry to interface with the IMD. Typically, the CPU 1204 includes the ability to process or monitor input signals (e.g., data) as controlled by program code stored in memory (e.g., ROM 1206).

The modules in the processor module 1204 that monitor arrhythmias and CO include an arrhythmia monitoring module 1270, the impedance detection module 1272, an HDP assessment module 1274 and a therapy module 1276. The arrhythmia monitoring module 1270 determines segment variations such as ST segment variations and changes in the amplitude and rate of the R-wave. The impedance detection module 1272 measures and/or calculates one or more of the first, second and third ECI impedance vectors Z1, Z2 and Z3. The HDP assessment module 1274 monitors the CO condition based on changes in the impedance vectors monitored by the impedance detection module 1272. The therapy control module 1276 assesses and determines what therapy to deliver. The therapy control module 1276 declaring ICI based therapies, IEGM based therapies and ECI based therapies. The therapy control module 1276 over-ruling and confirming ICI based therapy and non-therapy judgments utilizing ECI information.

The display 1224 (e.g., may be connected to a video display 1234) and the touch screen 1226 display text, alphanumeric information, data and graphic information via a series of menu choices to be selected by the user relating to the IMD 100, such as for example, status information, operating parameters, ECI parameters, CO parameters, therapy parameters, patient status, access settings, software programming version, ST segment thresholds, impedance thresholds, CO thresholds, other thresholds, and the like. The touch screen 1226 accepts a user's touch input 1236 when selections are made. The keyboard 1228 (e.g., a typewriter keyboard 1238) allows the user to enter data to the displayed fields, operational parameters, therapy parameters, as well as interface with the telemetry subsystem 1232. Furthermore, custom keys 1230 turn on/off 1240 (e.g., EVVI) the external device 1200. The printer 1214 prints hard-copies of reports 1242 for a physician/healthcare worker to review or to be placed in a patient file, and speaker 1212 provides an audible warning (e.g., sounds and tones 1244) to the user in the event a patient has any abnormal physiological condition occur while the external device 1200 is being used. The parallel I/O circuit 1220 interfaces with a parallel port 1246. The serial I/O circuit 1222 interfaces with a serial port 1248. The floppy drive 1218 accepts diskettes 1250. The CD-ROM drive 1216 accepts CD ROMs 1252.

The telemetry subsystem 1232 includes a central processing unit (CPU) 1254 in electrical communication with a telemetry circuit 1256, which communicates with both an ECG circuit 1258 and an analog out circuit 1260. The ECG circuit 1258 is connected to ECG leads 1262. The telemetry circuit 1256 is connected to a telemetry wand 1264. The analog out circuit 1260 includes communication circuits, such as a transmitting antenna, modulation and demodulation stages (not shown), as well as transmitting and receiving stages (not shown) to communicate with analog outputs 1266. The external device 1200 may wirelessly communicate with the IMD 100 and utilize protocols, such as Bluetooth, GSM, infrared wireless LANs, HIPERLAN, 3G, satellite, as well as circuit and packet data protocols, and the like. A wireless RF link utilizes a carrier signal that is selected to be safe for physiologic transmission through a human being and is below the frequencies associated with wireless radio frequency transmission. Alternatively, a hard-wired connection may be used to connect the external device 1200 to IMD 100 (e.g., an electrical cable having a USB connection).

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §32, sixth paragraph, unless and until such claim limitations expressly use the phrase "means for" followed by a statement of function void of further structure.

What is claimed is:

1. An implantable medical device, comprising:
at least one lead configured to be located proximate to a heart, the at least one lead including electrodes, at least a portion of the electrodes configured to sense cardiac activity;
a therapy module configured to control delivery of pacing pulses in accordance with a therapy timing and based on the cardiac activity sensed;
cardiac impedance (CI) sensor circuitry configured to be coupled to at least a first combination of the electrodes to sense cardiac impedance (CI), the CI sensor circuitry generating an impedance data stream associated with a corresponding CI sensing vector;
a CI module configured to manage the CI sensor circuitry to collect impedance data during active CI collection windows; and
an artifact reduction (AR) module configured to
shift at least one of i) the therapy timing of the therapy module or ii) the active CI collection windows forward or backward, to avoid delivery of the pacing pulses during the active CI collection windows during which the CI sensor circuitry collects impedance data.

2. The device of claim 1, wherein the CI module is configured to manage the CI sensor circuitry by turning the CI sensor circuitry ON and OFF during periodic sample intervals, each of the sample intervals having an active segment in which the CI sensor circuitry is ON and generates a corresponding sample sub-set of the impedance data, each of the sample intervals having an inactive segment in which the CI sensor circuitry is OFF and does not generate the impedance data, the CI module processing the impedance data collected over at least one cardiac cycle to provide an impedance sample set for the at least one cardiac cycle.

3. The device of claim 1, wherein the therapy module is configured to control discharge of a coupling capacitor electrically connected in series with a first electrode that delivers the pacing pulses, the therapy module managing a time at which the coupling capacitor discharges to interleave discharge of the coupling capacitor between active segments of the sample interval.

4. The device of claim 1, wherein the AR module is configured to shift the therapy timing to interleave the pacing pulses between the active CI collection windows.

5. The device of claim 1, wherein the wherein the AR module is configured to manage the active CI collection windows by shifting the active CI collection windows relative to the pacing pulses to avoid overlap of the pacing pulses and the active CI collection windows.

6. The device of claim 1, wherein the CI sensor circuitry is configured to turn ON and OFF during periodic sample intervals, each of the sample intervals having an active segment in which a sample sub-set of the impedance data is collected, each of the sample intervals having an inactive segment in which sample sub-sets are not collected, the therapy module managing a time at which a coupling capacitor discharges to overlap discharge of the coupling capacitor with the inactive segments of the sample intervals.

7. The device of claim 6, wherein the coupling capacitor accumulates a coupling charge in connection with delivery of the pacing pulse, the therapy module controlling the coupling capacitor to discharge the coupling charge in a separated divided manner over multiple inactive segments of the sample intervals.

8. An implantable medical device, comprising:
at least one lead configured to be located proximate to a heart, the at least one lead including electrodes, at least a portion of the electrodes configured to sense cardiac activity;
a therapy module configured to control delivery of pacing pulses in accordance with a therapy timing and based on the cardiac activity sensed;
cardiac impedance (CI) sensor circuitry configured to be coupled to at least a first combination of the electrodes to sense cardiac impedance (CI), the CI sensor circuitry generating an impedance data stream associated with a corresponding CI sensing vector;
a CI module configured to manage the CI sensor circuitry to collect impedance data during active CI collection windows, wherein the CI sensor circuitry is configured to turn ON and OFF during periodic sample intervals, each of the sample intervals having an active segment in which a sample sub-set of the impedance data is collected, each of the sample intervals having an inactive segment in which sample sub-sets are not generate, the therapy module managing a time at which the pacing pulse is delivered to interleave the pacing pulse between active segments of the sample interval; and an artifact reduction (AR) module configured to at least one of:
A) manage at least one of i) the therapy timing of the therapy module and ii) the active CI collection windows, to avoid delivery of the pacing pulses during the active CI collection windows during which the CI sensor circuitry collects impedance data; and
B) identify a reconstruction region in the impedance data and reconstruct a sample sub-set of the impedance data that occurs during the reconstruction region to at least partially remove artifacts in the impedance data stream associated with a pacing pulse.

9. The device of claim 8, wherein the AR module designates a beginning of the reconstruction region based on a time at which a corresponding pacing pulse is delivered, the reconstruction region having a predetermined artifact duration, the artifacts caused by at least one of i) the pacing pulses and ii) the coupling capacitor discharge.

10. The device of claim 8, wherein the artifacts are caused by at least one of i) the pacing pulses and ii) the coupling capacitor discharge and the reconstruction region has an artifact duration based on at least one of a width of the pacing pulse, a blanking interval following the pacing pulse, and a coupling capacitor discharge interval associated with the pacing pulse.

11. The device of claim 8, wherein the AR module is configured to replace the sample sub-set of the impedance data, that occurs during the reconstruction region, with a synthetic sample sub-set by at least one of:
A) applying a polynomial fit equation that connects valid sample sub-sets before and after the reconstruction region to bridge the reconstruction region;
B) applying interpolation to connect valid sample sub-sets before and after the reconstruction region to bridge the reconstruction region; and
C) applying a sinusoidal curve fitting filter to the impedance data before, within and after the reconstruction regions.

12. The device of claim 8, wherein the AR module is configured to apply at least one of high and low pass filters to the impedance data, the at least one of high and low pass filters having filter characteristics configured to at least partially correct for artifacts in the sample sub-set collected while delivering a pacing pulse.

13. A method for processing impedance data sensed by an implantable medical device (IMD), the IMD having at least one lead configured to be located proximate to a heart, the at least one lead including electrodes, at least a portion of the electrodes configured to sense cardiac activity, the method comprising:
controlling delivery of pacing pulses in accordance with a therapy timing and based on cardiac activity sensed;
providing cardiac impedance (CI) sensor channel configured to be coupled to at least a first combination of the electrodes to sense cardiac impedance (CI);
generating an impedance data stream, over the CI sensor channel, associated with a corresponding CI sensing vector;
managing the CI sensor channel to collect impedance data during active CI collection windows; and
performing artifact reduction (AR) by
shifting at least one of i) the therapy timing of the therapy module or ii) the active CI collection windows forward or backward, to avoid delivery of the pacing pulses during the active CI collection windows during which the CI sensor channel collects impedance data.

14. The method of claim 13, further comprising controlling discharge of a coupling capacitor electrically connected in series with a first electrode that delivers the pacing pulses, and managinge a time at which the coupling capacitor discharges to interleave discharge of the coupling capacitor between active segments of the sample interval.

15. The method of claim 13, further comprising shifting the therapy timing to interleave the pacing pulses between the active CI collection windows.

16. The method of claim 13, wherein the active CI collection windows is managed by shifting the active CI collection windows relative to the pacing pulses to avoid overlap of the pacing pulses and the active CI collection windows.

* * * * *